United States Patent
Kim

(10) Patent No.: US 10,631,834 B2
(45) Date of Patent: Apr. 28, 2020

(54) ULTRASOUND DIAGNOSIS APPARATUS AND COMMUNICATION CONNECTING METHOD PERFORMED IN THE ULTRASOUND DIAGNOSIS APPARATUS

(71) Applicant: SAMSUNG ELECTRONICS CO., LTD., Suwon-si (KR)

(72) Inventor: Hang-chan Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 892 days.

(21) Appl. No.: 14/799,203

(22) Filed: Jul. 14, 2015

(65) Prior Publication Data

US 2016/0100824 A1  Apr. 14, 2016

(30) Foreign Application Priority Data

Oct. 8, 2014 (KR) .......................... 10-2014-0135956

(51) Int. Cl.
*A61B 8/00* (2006.01)
*G06F 19/00* (2018.01)
(Continued)

(52) U.S. Cl.
CPC .............. *A61B 8/565* (2013.01); *A61B 8/13* (2013.01); *A61B 8/4427* (2013.01); *A61B 8/4472* (2013.01); *A61B 8/461* (2013.01); *A61B 8/54* (2013.01); *G06F 19/321* (2013.01); *G06F 19/3418* (2013.01); *G16H 40/63* (2018.01)

(58) Field of Classification Search
CPC .............. A61B 8/00; A61B 8/13; A61B 8/565
See application file for complete search history.

(56) References Cited

U.S. PATENT DOCUMENTS

| 6,497,661 B1 | 12/2002 | Brock-Fisher |
| 2002/0016545 A1 | 2/2002 | Quistagaard et al. |
| (Continued) | | |

FOREIGN PATENT DOCUMENTS

| EP | 2617360 A1 | 7/2013 |
| EP | 2889003 A1 | 7/2015 |
| (Continued) | | |

OTHER PUBLICATIONS

Communication dated Mar. 29, 2017 issued by the Korean Intellectual Property Office in counterpart Korean Patent Application No. 10-2014-0135956, English Translation.
(Continued)

*Primary Examiner* — Joel F Brutus
(74) *Attorney, Agent, or Firm* — Sughrue Mion, PLLC

(57) ABSTRACT

An ultrasound diagnosis apparatus which is connectable to a wireless probe that acquires first data by scanning an object is provided. The ultrasound diagnosis apparatus includes a controller which is configured to recognize an occurrence of a first event, to automatically terminate a first communication connection to the wireless probe via a first communication network, and to control an automatic start of a second communication connection to an external apparatus via the first communication network; and a communicator which is configured to exchange data with the wireless probe and/or with the external apparatus by using the first communication network under the control of the controller.

17 Claims, 12 Drawing Sheets

(51) Int. Cl.
*G16H 40/63* (2018.01)
*A61B 8/13* (2006.01)

(56) References Cited

U.S. PATENT DOCUMENTS

| | | |
|---|---|---|
| 2005/0215900 A1 | 9/2005 | Kim |
| 2008/0114247 A1* | 5/2008 | Urbano ............... A61B 8/4472 600/447 |
| 2009/0043199 A1 | 2/2009 | Pelissier et al. |
| 2011/0218436 A1 | 9/2011 | Dewey et al. |
| 2012/0179037 A1 | 7/2012 | Halmann |
| 2013/0114380 A1 | 5/2013 | Bryger et al. |
| 2013/0184587 A1* | 7/2013 | Eom ............... A61B 8/4411 600/443 |
| 2013/0215277 A1 | 8/2013 | Kang |
| 2013/0226001 A1 | 8/2013 | Steen et al. |
| 2014/0180110 A1 | 6/2014 | Schmedling |
| 2014/0240123 A1* | 8/2014 | Lee ............... G08B 21/02 340/539.12 |
| 2015/0297180 A1 | 10/2015 | Lee et al. |

FOREIGN PATENT DOCUMENTS

| | | |
|---|---|---|
| JP | 2007282957 A | 11/2007 |
| JP | 2010167209 A | 8/2010 |
| JP | 2011236 A | 1/2011 |
| KR | 10-2012-0124123 A | 11/2012 |
| KR | 10-2013-0084467 A | 7/2013 |
| KR | 10-2014-0026289 A | 3/2014 |
| KR | 10-2014-0089328 A | 7/2014 |
| KR | 1020140111543 A | 9/2014 |
| WO | 2014/030933 A1 | 2/2014 |

OTHER PUBLICATIONS

Communication dated Sep. 9, 2016, issued by the Korean Intellectual Property Office in counterpart Korean Application No. 10-2014-0135956.
Communication dated Jan. 11, 2016, issued by the Korean Intellectual Property Office in counterpart Korean Patent Application No. 10-2014-0135956.
Search Report dated Jan. 22, 2016, issued by the International Searching Authority in counterpart International Patent Application No. PCT/KR2015/010439 (PCT/ISA/210).
Written Opinion dated Jan. 22, 2016, issued by the International Searching Authority in counterpart International Patent Application No. PCT/KR2015/010439 (PCT/ISA/237).
Communication dated Mar. 4, 2016, issued by the European Patent Office in counterpart European Patent Application No. 15181608.9.
Communication dated Feb. 28, 2018, issued by the European Patent Office in counterpart European Application No. 15181608.9.
Communication dated Oct. 29, 2018, from the European Patent Office in counterpart European Application No. 15181608.9.
Communication dated Dec. 12, 2019 issued by the Indian Intellectual Property Office in Indian counterpart Application No. 2905/DEL/2015.

* cited by examiner

ULTRASOUND DIAGNOSIS APPARATUS AND COMMUNICATION CONNECTING METHOD PERFORMED IN THE ULTRASOUND DIAGNOSIS APPARATUS

RELATED APPLICATION

This application claims priority from Korean Patent Application No. 10-2014-0135956, filed on Oct. 8, 2014, in the Korean Intellectual Property Office, the disclosure of which is incorporated herein by reference in its entirety.

BACKGROUND

1. Field

One or more exemplary embodiments relate to an ultrasound diagnosis apparatus and a communication connecting method performed in the ultrasound diagnosis apparatus.

More particularly, one or more exemplary embodiments relate to an ultrasound diagnosis apparatus that transmits and/or receives data to or from a wireless probe and an external apparatus via a wireless communication network and a communication connecting method performed in the ultrasound diagnosis apparatus.

2. Description of the Related Art

Ultrasound diagnosis apparatuses transmit an ultrasound signal generated by a transducer of a wireless probe to an object and receive an ultrasound echo signal reflected from the object, thereby obtaining an image of a part inside the object. In particular, ultrasound diagnosis apparatuses are used for medical purposes, such as observation of the inside of an object, detection of foreign substances inside the object, and diagnosis of damage thereof. Such ultrasound diagnosis apparatuses have various advantages, including stability, real-time display, and safety because there is no exposure to radiation, as compared with X-ray apparatuses, and thus, the ultrasound diagnosis apparatuses are commonly used together with other image diagnosis apparatuses.

Portable ultrasound diagnosis apparatuses and wireless probes have been developed to facilitate determination of diagnosis of patients, without any spatial restrictions. Ultrasound images and data related with ultrasound diagnosis that are acquired by a portable ultrasound diagnosis apparatus may be transmitted to an external apparatus and may be used thereby. The external apparatus may include a computing device and/or a server of a hospital, and/or any of other medical diagnosis apparatuses, or the like.

A wireless probe may obtain data by scanning an object, and transmit the data to a portable ultrasound diagnosis apparatus via wireless communication. The portable ultrasound diagnosis apparatus may transmit the data obtained by the wireless probe to an external apparatus via wireless communication. The data obtained by the wireless probe may be ultrasound data which corresponds to ultrasound echo signals acquired by scanning an object by using ultrasound waves, or may be an ultrasound image generated using an ultrasound echo signal.

Wireless probes that are connected to ultrasound diagnosis apparatuses via wireless networks have been being developed to enable a user to manipulate a probe, without any spatial restrictions.

In this case, a wireless probe, an ultrasound diagnosis apparatus, and an external apparatus need to be quickly and conveniently connected to one another via wireless communication in order to increase convenience for users.

SUMMARY

One or more exemplary embodiments include an ultrasound diagnosis apparatus which is capable of easily performing wireless communication with a wireless probe and an external apparatus, and a communication connecting method performed in the ultrasound diagnosis apparatus.

One or more exemplary embodiments also include a wireless probe and an external apparatus which are capable of increasing user convenience and easiness when an ultrasound diagnosis apparatus performs wireless communication with the wireless probe and the external apparatus.

Additional aspects will be set forth in part in the description which follows and, in part, will be apparent from the description, or may be learned by practice of the presented exemplary embodiments.

According to one or more exemplary embodiments, an ultrasound diagnosis apparatus is connectable to a wireless probe that acquires first data by scanning an object. The ultrasound diagnosis apparatus includes a controller which is configured to recognize an occurrence of a first event, to automatically terminate a first communication connection to the wireless probe via a first communication network, and to control an automatic start of a second communication connection to an external apparatus via the first communication network; and a communicator which is configured to exchange data with the wireless probe and/or with the external apparatus by using the first communication network under a control of the controller.

The occurrence of the first event may be based on an operational status of at least one from among the wireless probe, the ultrasound diagnosis apparatus, and the external apparatus.

The first event may occur when the first data is not received by the ultrasound diagnosis apparatus after the first data has been acquired by the wireless probe.

The first event may occur when a determination that the ultrasound diagnosis apparatus does not need to receive the first data is made.

The first event may occur when the wireless probe fails to scan the object.

The ultrasound diagnosis apparatus may further include a display which is configured to display an ultrasound image which corresponds to the first data.

The first event may occur when the display of the ultrasound image terminates.

The first event may occur when a manipulation of a user is not sensed for at least a predetermined period of time.

The first event may occur when the ultrasound diagnosis apparatus enters a standby mode.

The communicator may be further configured to receive the first data in real time, and the first event may occur when the display displays a screen image which does not include the ultrasound image which corresponds to the first data.

The first event may occur when the display displays a still image.

The first event may occur when an ultrasound diagnosis of the object terminates.

The ultrasound diagnosis apparatus may further include a user interface (UI) device which is configured to receive a user input.

The first event may occur based on a user request that is received via the UI device.

The first event may occur in response to a scanning stop request that is received via the UI device.

The first event may occur in response to a request to transmit data to the external apparatus, which is received via the UI device.

The first event may occur in response to a request to terminate transmission of the first data, which is received via the wireless probe.

The first event may occur in response to a request to transmit data to the external apparatus, which is received via the wireless probe.

The first event may occur in response to a scanning stop request that is received via the wireless probe.

The ultrasound diagnosis apparatus may further include a memory which is configured to store the first data when the first data is received. The occurrence of the first event may correspond to at least one from among the memory storing the first data and a first ultrasound image which corresponds to the first data being generated under the control of the controller.

The ultrasound diagnosis apparatus may further include a memory which is configured to store the first data when the first data is received. The first event may occur in response to a request for a review mode in which a first ultrasound image which corresponds to the first data previously stored in the memory is displayed.

When the second communication connection starts, the controller may be further configured to transmit, to the external apparatus, the first data, and second data which includes at least one ultrasound image from among a plurality of first ultrasound images which correspond to the first data.

The ultrasound diagnosis apparatus may further include a memory which is configured to store termination information which includes at least one from among status information which relates to a communication with the wireless probe at a first point of time when the first communication connection terminates and information which relates to the received first data.

The controller may control, based on the termination information, data which is transmitted subsequent to data which was transmitted from the wireless probe to the communicator before the first point of time, so that the subsequent data is received.

When a second event occurs, the controller may be further configured to terminate the second communication connection and to restore the first communication connection in response to the occurrence of the second event.

The second event may occur when a determination is made that a data exchange between the ultrasound diagnosis apparatus and the wireless probe is necessary.

The occurrence of the second event may be based on an operational status of at least one from among the wireless probe, the ultrasound diagnosis apparatus, and the external apparatus.

The display may be further configured to display a UI screen image which relates to setting the second event.

When a transmission of the second data is completed, the controller may be further configured to terminate the second communication connection and to restart the first communication connection.

When a scanning stop request previously received by at least one from among the wireless probe and the ultrasound diagnosis apparatus is canceled, the controller may be further configured to terminate the second communication connection and to restore the first communication connection.

When a request to scan the object is received, the controller may be further configured to terminate the second communication connection and to restore the first communication connection.

When data exchange with the external apparatus is completed, the controller may be further configured to terminate the second communication connection and to restore the first communication connection.

When a medical worklist (MWL) is received from the external apparatus via the second communication connection, the controller may be further configured to terminate the second communication connection and to restore the first communication connection.

The external apparatus may include a medical diagnosis apparatus which is usable by a medical institution.

The first communication network may include a communication network which is based on at least one from among a wireless fidelity (Wi-Fi) communication standard and a Wi-Fi-direct (WFD) communication standard.

The communicator may include a first communication module configured to perform wireless communication based on the first communication network, and to establish each of the first communication connection and the second communication connection by using the first communication module.

The ultrasound diagnosis apparatus may further include a memory which is configured to store first setting information which relates to the first communication connection and to store second setting information which relates to the second communication connection. The communicator may be further configured to automatically start at least one from among the first communication connection and the second communication connection by using at least one from among the first setting information and the second setting information.

The controller may be further configured to start or maintain the first communication connection when an ultrasound image which corresponds to the first data is requested to be displayed, and to start or maintain the second communication connection when a determination that a display of the ultrasound image is not requested is made.

When the ultrasound diagnosis apparatus continues a data exchange with at least one from among the wireless probe and the external apparatus for at least a predetermined period of time, the controller may be further configured to control the data exchange to be conducted in a background environment.

The display may be further configured to display a UI screen image which relates to setting the first event.

According to one or more exemplary embodiments, a communication connecting method is performed in an ultrasound diagnosis apparatus which is connectable to a wireless probe that acquires first data by scanning an object. The communication connecting method includes recognizing an occurrence of a first event, automatically terminating a first communication connection to the wireless probe via a first communication network and automatically starting a second communication connection to an external apparatus via the first communication network; and exchanging data with at least one from among the wireless probe and the external apparatus via at least one from among the first communication connection and the second communication connection.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
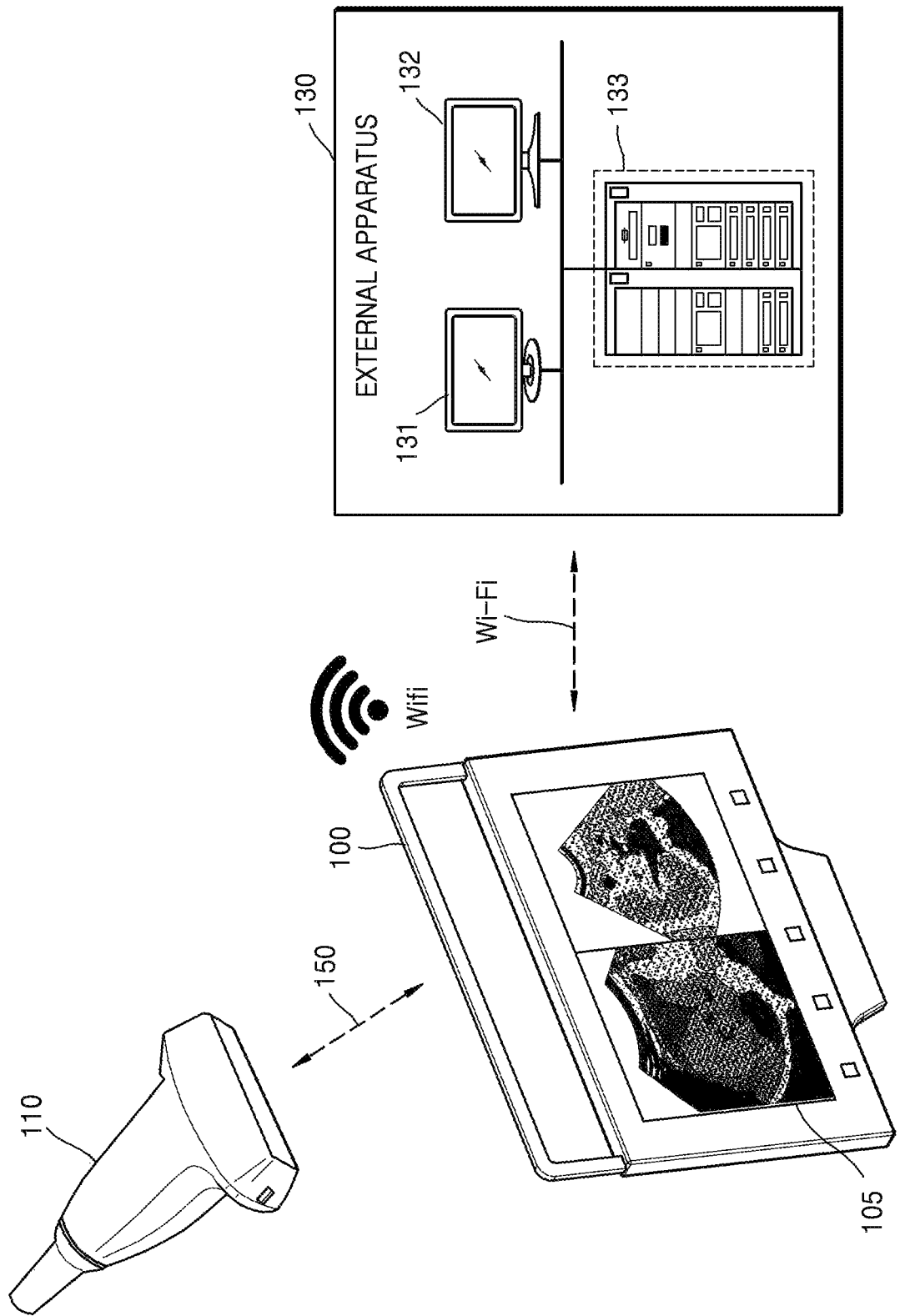
FIG. 1 illustrates an ultrasound diagnosis apparatus, and a wireless probe and an external apparatus connected to the ultrasound diagnosis apparatus.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

Although general terms widely used at present were selected for describing the exemplary embodiments in consideration of the functions thereof, these general terms may vary according to intentions of one of ordinary skill in the art, case precedents, the advent of new technologies, and the like. Terms arbitrarily selected by the applicant may also be used in a specific case. In this case, their meanings must be given in the detailed description. Hence, the terms must be defined based on their meanings and the contents of the entire specification, not by simply stating the terms.

The terms "comprises" and/or "comprising" or "includes" and/or "including" when used in this specification, specify the presence of stated elements, but do not preclude the presence or addition of one or more other elements. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object that is acquired using ultrasound waves. Furthermore, an "object" may include a human, an animal, or a part of a human or animal. For example, the object may include an organ (for example, the liver, the heart, the womb, the brain, breasts, or the abdomen), blood vessels, or a combination thereof. The object may be a phantom. The phantom means a material having a density, an effective atomic number, and a volume that are approximately the same as those of a living thing.

Throughout the specification, a "user" may include, but is not limited to, a medical professional, such as a medical doctor, a nurse, a medical laboratory technologist, a medical image expert, and an engineer who repairs a medical apparatus.

Exemplary embodiments now will be described more fully hereinafter with reference to the accompanying drawings.

FIG. 1 illustrates an ultrasound diagnosis apparatus 100, and a wireless probe 110 and an external apparatus 130 connected to the ultrasound diagnosis apparatus 100.

Referring to FIG. 1, the ultrasound diagnosis apparatus 100 may be connected to the wireless probe 110 and/or to the external apparatus 130 via a wireless communication network.

In detail, the wireless probe 110 is wirelessly connected to the ultrasound diagnosis apparatus 100 via a network 150 and scans an object with ultrasound waves. In detail, the wireless probe 110 acquires ultrasound data by transmitting an ultrasound signal toward the object and receiving an ultrasound echo signal reflected by the object. The wireless probe 110 may generate an ultrasound image by using the acquired ultrasound data and transmit the ultrasound image to the ultrasound diagnosis apparatus 100. Alternatively, the wireless probe 110 may transmit the acquired ultrasound data to the ultrasound diagnosis apparatus 100 without generating an ultrasound image. In this case, the ultrasound diagnosis apparatus 100 may generate the ultrasound image by using the received ultrasound data.

Data acquired by the wireless probe 110 by scanning an object will now be referred to as first data. The first data may include at least one from among the ultrasound echo signal, the ultrasound data generated based on the ultrasound echo signal, and the ultrasound image generated using the ultrasound data.

The ultrasound diagnosis apparatus 100 is an electronic apparatus which is capable of using, processing, and displaying the ultrasound image. In detail, the ultrasound diagnosis apparatus 100 includes any one or more of apparatuses that are capable of using, processing, and displaying the ultrasound image, and may also include software or applications provided therein.

The ultrasound diagnosis apparatus 100 may generate ultrasound images of any of various modes by using the first data received from the wireless probe 110. The ultrasound diagnosis apparatus 100 may control an operation of the wireless probe 110, based on a user input.

The ultrasound diagnosis apparatus 100 may be implemented by using a portable apparatus that does not have space restraints. In detail, the ultrasound diagnosis apparatus 100 may be a portable ultrasound diagnosis apparatus or a portable computing device. Alternatively, the ultrasound diagnosis apparatus 100 may be implemented by using a cart type apparatus. Examples of the ultrasound diagnosis apparatus 100 may include, but are not limited to, a picture archiving and communication system (PACS) viewer, a smartphone, a laptop computer, a personal digital assistant (PDA), and a tablet personal computer (PC).

The ultrasound diagnosis apparatus 100 may also be connected to the external apparatus 130, which is an externally connected computing device, via a network 160, and may transmit the first data and/or an image or data generated based on the first data to the external apparatus 130. The network 160 may be a wired or wireless communication network. The network 160 may be a wireless communication network so that the ultrasound diagnosis apparatus 100 may be used without having space restraints.

The external apparatus 130 receives the first data and/or an ultrasound image which corresponds to the first data and stores, processes, and/or utilizes the received first data or ultrasound image. Thus, the external apparatus 130 may include any one or more of a medical imaging apparatus, a medical server, a portable terminal, and/or any computing device capable of utilizing and processing medical images. For example, the external apparatus 130 may be a medical diagnosis apparatus which is usable by a medical institution, such as a hospital. For example, the external apparatus 130 may include a server which is used by a hospital for recoding and storing medical treatment histories of patients, and/or a medical imaging apparatus used by medical doctors in a hospital to read medical images.

FIG. 1 illustrates a case in which the external apparatus 130 includes medical imaging apparatuses 131 and 132 capable of utilizing and processing medical images, and a medical server 133.

The wireless probe 110 may be a wireless probe that performs only a scan operation, as illustrated in FIG. 1. The ultrasound diagnosis apparatus 100 may be a portable apparatus which is designed to overcome space restraints imposed on a user when using the ultrasound diagnosis apparatus 100. In FIG. 1, the ultrasound diagnosis apparatus 100 is a portable ultrasound diagnosis apparatus.

Figure 2:
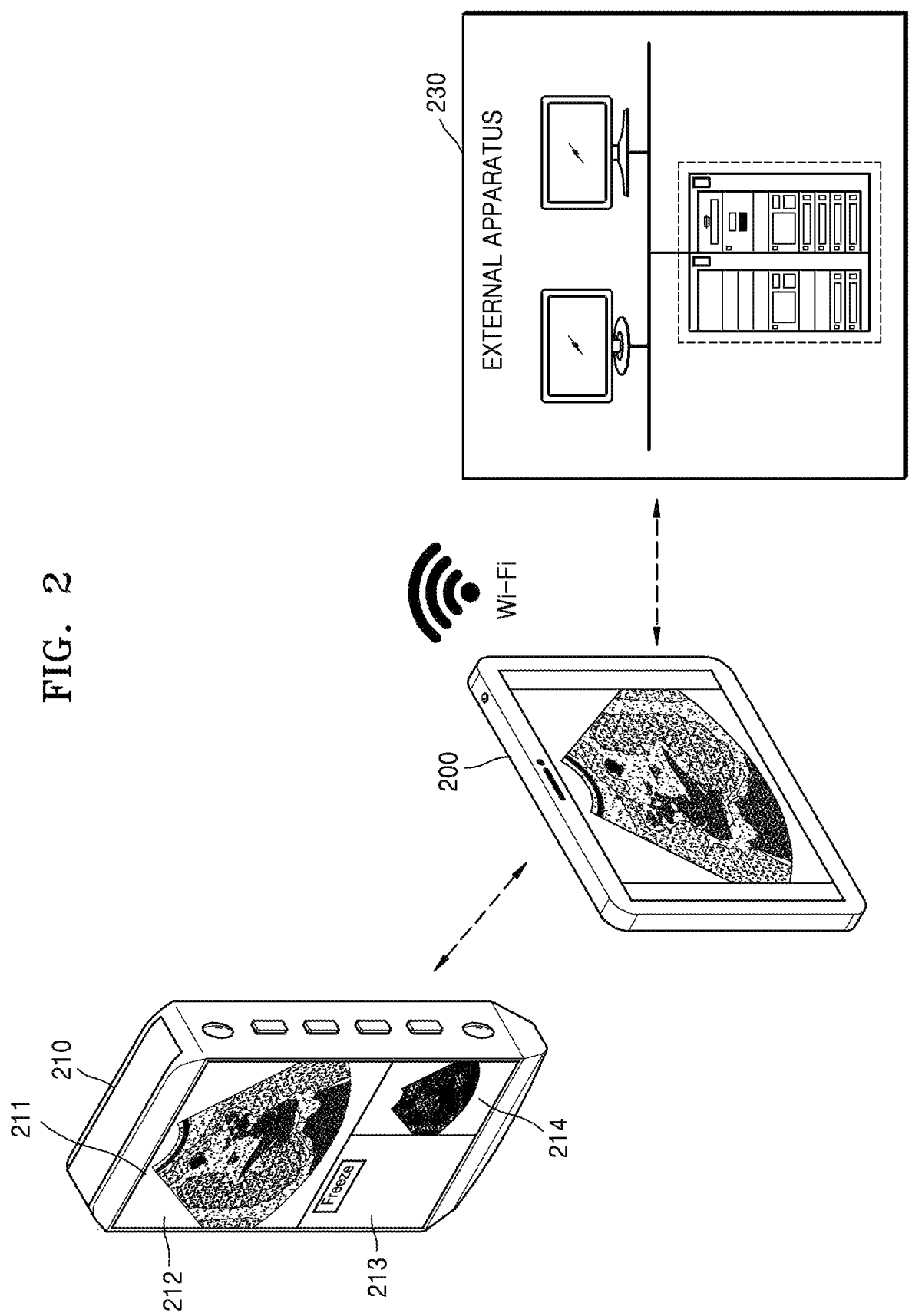
FIG. 2 illustrates another ultrasound diagnosis apparatus, and another wireless probe and another external apparatus connected to the ultrasound diagnosis apparatus.

FIG. 2 illustrates an ultrasound diagnosis apparatus 200, and a wireless probe 210 and an external apparatus 230, both of which are connected to the ultrasound diagnosis apparatus 200. The wireless probe 210, the ultrasound diagnosis apparatus 200, and the external apparatus 230 of FIG. 2 are respectively the same as the wireless probe 110, the ultrasound diagnosis apparatus 100, and the external apparatus 130 of FIG. 1, and thus repeated descriptions thereof will be omitted.

The wireless probe 210 may be a smart device that includes a transducer array and is configured to perform a scan operation. In detail, the wireless probe 210 may be a smart device which is capable of scanning an object by using a transducer array included therein to acquire ultrasound data, generating an ultrasound image by using the ultrasound data, and/or displaying the ultrasound image. For example, the wireless probe 210 may include a display 211, and may display, via the display 211, a screen image which includes at least one ultrasound image, namely, ultrasound images 212 and 214, and/or a user interface (UI) screen image 213 for facilitating user control of an object-scan operation.

In FIGS. 1 and 2, the ultrasound diagnosis apparatuses 100 and 200 may be connected to the wireless probes 110 and 210 and/or to the external apparatuses 130 and 230, respectively, via wireless networks. Each of the wireless networks may follow an identical communication standard. Examples of the wireless networks may include, but are not limited to, Wi-Fi, Bluetooth, ZigBee, Wi-Fi Direct (WFD), ultra wideband (UWB), infrared data association (IrDA), Bluetooth low energy (BLE), and near field communication (NFC).

FIGS. 1 and 2 illustrate cases where the ultrasound diagnosis apparatuses 100 and 200 are respectively connected to the wireless probes 110 and 210 and/or to the external apparatuses 130 and 230 via a WiFi network.

Referring back to FIG. 1, while a user is scanning a predetermined body part of a patient, which is an object, by using the wireless probe 110, the wireless probe 110 and the ultrasound diagnosis apparatus 100 may continuously transmit or receive certain data to or from each other via the wireless network 150. In detail, while a user is scanning a predetermined body part of a patient, which is an object, by using the wireless probe 110, the wireless probe 110 may transmit the first data to the ultrasound diagnosis apparatus 100 via the wireless network 150 in real time. In detail, the first data may be updated in real time as ultrasound scanning continues, and may be transmitted from the wireless probe 110 to the ultrasound diagnosis apparatus 100.

Then, the ultrasound diagnosis apparatus 100 may receive the first data, and process and display an ultrasound image which corresponds to the received first data in real time. In particular, when the first data is updated and transmitted in real time, the ultrasound diagnosis apparatus 100 may display a first ultrasound image that is updated in real time. Moreover, to achieve recording and utilization of the first data or the ultrasound image corresponding to the first data, the ultrasound diagnosis apparatus 100 must transmit at least one selected from the first data and the ultrasound image to the external apparatus 130.

When the ultrasound diagnosis apparatus 100 communicates with the wireless probe 110 and the external apparatus 130 by using a single communication module that follows an identical communication standard, the ultrasound diagnosis apparatus 100 is not able to simultaneously exchange data with the wireless probe 110 and the external apparatus 130. For example, if the ultrasound diagnosis apparatus 100 includes only one Wi-Fi communication module based on the Wi-Fi communication standard, when the ultrasound diagnosis apparatus 100 communicates with the wireless probe 110 by using the Wi-Fi communication module, the ultrasound diagnosis apparatus 100 is unable to communicate with the external apparatus 130 via the Wi-Fi communication module. Thus, in order to enable the ultrasound diagnosis apparatus 100 to transmit the first data and/or the ultrasound image corresponding to the first data received from the wireless probe 110 to the external apparatus 130, a user must stop the communication connection between the wireless probe 110 and the ultrasound diagnosis apparatus 100 by manually manipulating the ultrasound diagnosis apparatus 100, and then start a communication connection between the ultrasound diagnosis apparatus 100 and the external apparatus 130.

While a patient is being scanned, a user connects the wireless probe 110 to the ultrasound diagnosis apparatus 100 so that first data acquired as a result of to the scanning is transmitted to the ultrasound diagnosis apparatus 100. When the scanning is completed, the user must connect the ultrasound diagnosis apparatus 100 to the external apparatus 130 so that the first data is transmitted from the ultrasound diagnosis apparatus 100 to the external apparatus 130. The user performs scan operations on several dozens of patients a day, and is inconvenienced by having to manually perform such a communication connection change for each of the scan operations on the several dozens of patients.

Therefore, the ultrasound diagnosis apparatus 100 should quickly and easily transmit the first data received from the wireless probe 110 and/or second data which is acquired based on the first data to the external apparatus 130, in order to increase the convenience for users. Ultrasound diagnosis apparatuses according to exemplary embodiments that are connected to wireless probes or external apparatuses via wireless networks and are capable of conveniently exchanging data therewith will now be described in detail with reference to FIGS. 3-12.

Figure 3:
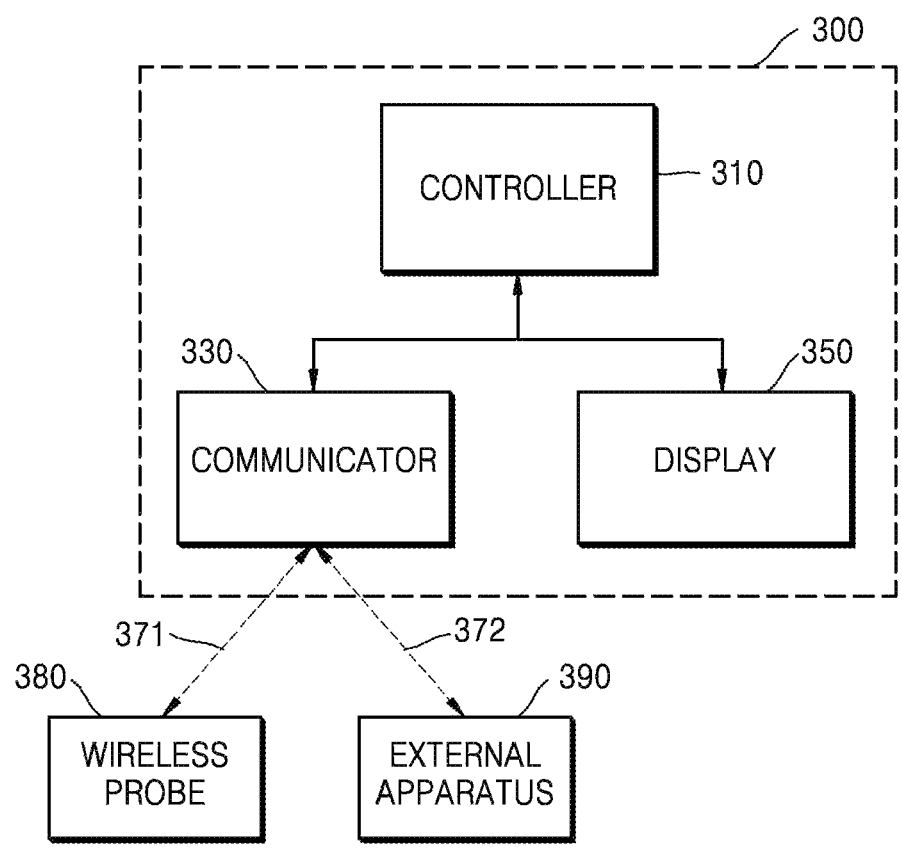
FIG. 3 is a block diagram of an ultrasound diagnosis apparatus, according to an exemplary embodiment.

FIG. 3 is a block diagram of an ultrasound diagnosis apparatus 300, according to an exemplary embodiment.

Referring to FIG. 3, the ultrasound diagnosis apparatus 300 is the same as each of the ultrasound diagnosis apparatuses 100 and 200 of FIGS. 1 and 2. A wireless probe 380 and an external apparatus 390 of FIG. 3 respectively correspond to each of the wireless probes 110 and 210 and each of the external apparatuses 130 and 330 of FIGS. 1 and 2. Accordingly, descriptions of the ultrasound diagnosis apparatus 300 that are the same as those made with reference to FIGS. 1 and 2 are not repeated herein.

The ultrasound diagnosis apparatus 300 may be connected to the wireless probe 380 which acquires first data by scanning an object, and thus may perform an ultrasound imaging operation. The ultrasound diagnosis apparatus 300 includes a controller 310 and a communicator 330. The ultrasound diagnosis apparatus 300 may further include a display 350.

When a first event occurs, the controller 310 recognizes the occurrence of the first event, and thus automatically terminates a first communication connection 371 to the wireless probe 380 via a first communication network and controls a second communication connection 372 to the external apparatus 390 via the first communication network to automatically start.

The first communication connection 371 denotes a wireless communication connection between the ultrasound diagnosis apparatus 300 and the wireless probe 380, and the second communication connection 372 denotes a wireless communication connection between the ultrasound diagnosis apparatus 300 and the external apparatus 390. There is no limitation in the communication standards applied to the first communication connection 371 and the second communication connection 372, and any of various communication standards other than the first communication network may be applied. However, in the present exemplary embodiment, a case where the first communication connection 371 and the second communication connection 372 are performed via communication networks that follow an identical communication standard is illustrated.

In detail, the controller 310 may automatically terminate the first communication connection 371 and control the second communication connection 372 to automatically start, in response to the first event. In particular, when the first event occurs, the controller 310 may automatically terminate the first communication connection 371 so that data exchange with the wireless probe 380 is stopped, and may control the second communication connection 372 to automatically start so that data exchange with the external apparatus 390 is performed.

The first event may occur based on an operational status of at least one selected from the wireless probe 380, the ultrasound diagnosis apparatus 300, and the external apparatus 390.

In detail, the first event may be an event which corresponds to a case in which the ultrasound diagnosis apparatus 300 is not required to communicate with the wireless probe 380. For example, the first event may occur when the first data is not received by the ultrasound diagnosis apparatus 300. Alternatively, the first event may occur when a determination is made that the ultrasound diagnosis apparatus 300 is not required to receive the first data.

The first event may occur based on the internal settings of the controller 310, a user input, an operation of a user, and/or at least one selected from among an operational status of the wireless probe 380, an operational status of the ultrasound diagnosis apparatus 300, and an operational status of the external apparatus 390. The first event will now be described in detail.

The first communication network is a wireless communication network for data exchange between the ultrasound diagnosis apparatus 300 and at least one selected from among the wireless probe 380 and the external apparatus 390. The first communication network may be a network which is based on the local area communication standard or a network which is based on the mobile-distance communication standard.

The communicator 330 transmits and/or receives data to and/or from the wireless probe 380 and/or the external apparatus 390 by using the first communication network under the control of the controller 310.

In detail, the communicator 330 may receive the first data from the wireless probe 380 via the first communication network and transmit, to the wireless probe 380, data which is usable for controlling an operation of the wireless probe 380. The first data may include data generated by the wireless probe 380 while scanning an object. In detail, the first data may include ultrasound echo signals that are received by transducer elements of the wireless probe 380 as the wireless probe 380 scans an object, or may include ultrasound data generated by processing an ultrasound echo signal. The first data may also include an ultrasound image generated by the ultrasound data or related data that is produced using the ultrasound data. In detail, the wireless probe 380 may transmit and/or receive, to or from the communicator 330, at least one selected from among an ultrasound echo signal, ultrasound data, an ultrasound image of an object, data according to modes, such as Doppler data, and data which relates to a diagnosis of the object.

The communicator 330 may transmit second data to the external apparatus 390 via the first communication network and receive third data from the external apparatus 390 via the first communication network. The second data may be data produced based on the first data transmitted by the wireless probe 380. In detail, the second data may include any one or more of an ultrasound image, ultrasound data, scan-related data, diagnosis data of a patient, and the like. The third data includes data transmitted by the external apparatus 390 to the ultrasound diagnosis apparatus 300. The third data may include any one or more of patient-related information, data necessary for diagnosing and treating patients, histories of previous treatments of patients, a medical worklist (MWL) corresponding to diagnosis instructions for patients, and the like. The third data may include a request and/or a command that is transmitted by the external apparatus 390 to the ultrasound diagnosis apparatus 300.

The communicator 330 may transmit and/or receive a medical image captured by the external apparatus 390, which is another medical apparatus such as a computed tomography (CT) apparatus, a magnetic resonance imaging (MRI) apparatus, or an X-ray apparatus. Furthermore, the communicator 330 may receive information about diagnosis histories and/or medical treatment schedules of patients from a server, and may utilize the received information in order to diagnose an object. In addition, the communicator 330 may perform data communication with the external apparatus 390, which is a portable terminal of a medical doctor or a patient, as well as the external apparatus 390, which is a server or medical apparatus of a hospital.

The communicator 330 may also exchange data with the external apparatus 390, which is a hospital server or a medical apparatus in a hospital, and which may be connected via a PACS. The communicator 330 may perform data communication according to the digital imaging and communications in medicine (DICOM) standard.

As described above, the ultrasound diagnosis apparatus 300 may further include the display 350. The display 350 displays a predetermined screen image. In detail, the display 350 displays a predetermined screen image under the control of the controller 310. In detail, the display 350 includes a display panel (not shown), and may display any one or more of a UI screen image, a medical image, and the like on the display panel.

A communication connection between the ultrasound diagnosis apparatus 300 and either the wireless probe 380 or the external apparatus 390 will now be described in detail with reference to FIG. 4.

Figure 4:
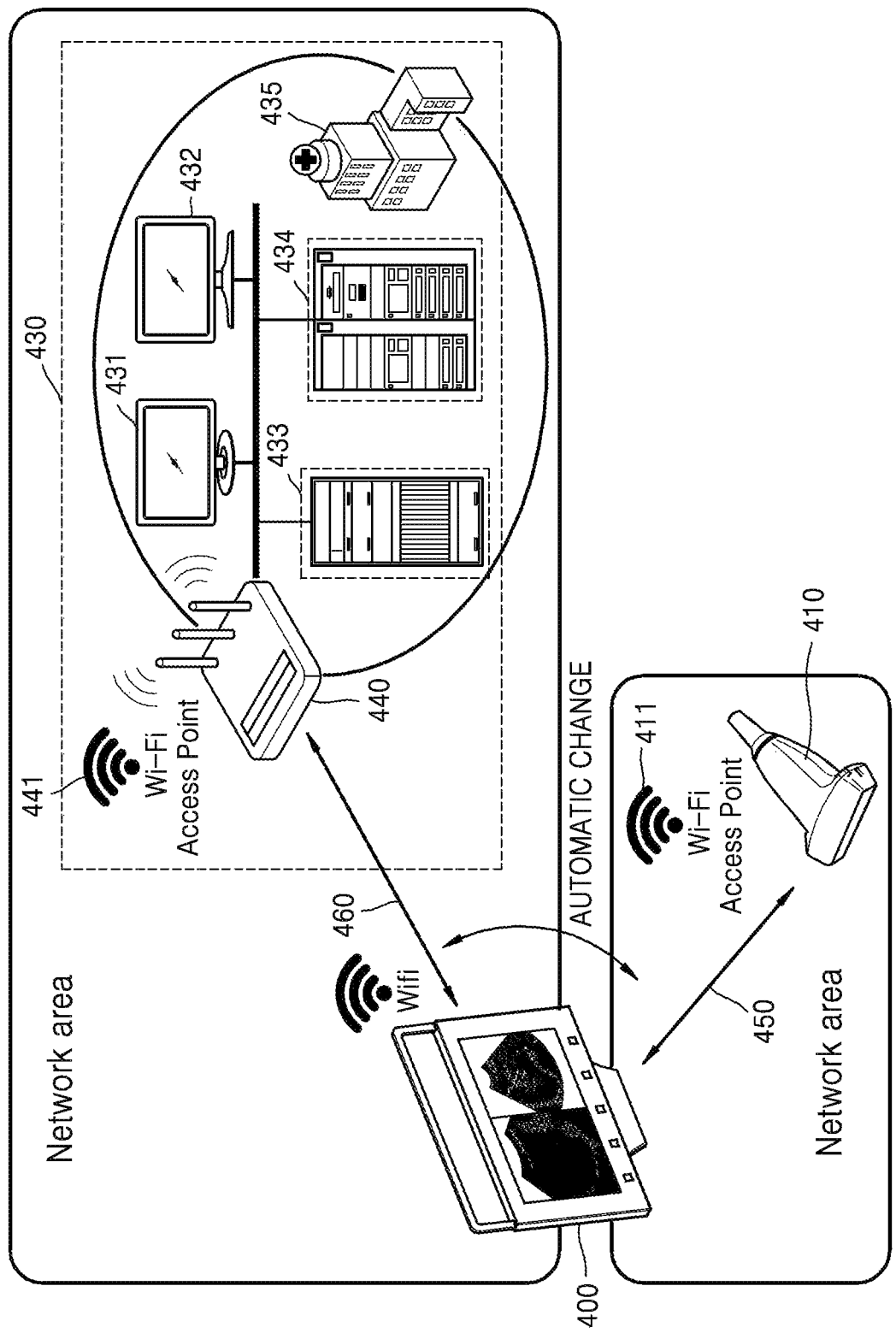
FIG. 4 illustrates an ultrasound diagnosis apparatus according to an exemplary embodiment and a wireless probe and an external apparatus that communicate with the ultrasound diagnosis apparatus.

FIG. 4 illustrates an ultrasound diagnosis apparatus 400 according to an exemplary embodiment, and a wireless probe 410 and an external apparatus 430 that communicate with the ultrasound diagnosis apparatus 400. The ultrasound diagnosis apparatus 400, the wireless probe 410, and the external apparatus 430 of FIG. 4 are respectively the same as the ultrasound diagnosis apparatus 300, the wireless probe 380, and the external apparatus 390 of FIG. 3, and thus repeated descriptions thereof will be omitted.

The external apparatus 430 may include any one or more of a computing device or a server of a hospital, a medical server, any of other medical diagnosis apparatuses, or the like. In detail, the external apparatus 430 may include any electronic apparatuses capable of receiving, storing, processing, or displaying at least one selected from among an ultrasound image, ultrasound data, and related information produced using the ultrasound image and the ultrasound data.

Referring to FIG. 4, the external apparatus 430 may include at least one selected from among display devices 431 and 432, a medical server 433, an image acquisition device included in a PACS, database 434, and an image display device (not shown), which are located in a hospital 435.

The ultrasound diagnosis apparatus 400 may be connected to the wireless probe 410 and/or to the external apparatus 430 via a Wi-Fi or WFD communication network. FIG. 4 illustrates a case where the ultrasound diagnosis apparatus 400 is connected to the wireless probe 410 and/or to the external apparatus 430 via a Wi-Fi network.

Examples of a wireless communication network via which the ultrasound diagnosis apparatus 400 can be connected to the wireless probe 410 or the external apparatus 430 may include, but are not limited to, wireless LAN, Wi-Fi, Bluetooth, ZigBee, WFD, UWB, IrDA, BLE, and NFC.

The controller 310 or a memory (not shown) included in the ultrasound diagnosis apparatus 400 may store network setting information used to perform a communication connection to an externally connected apparatus via a predetermined network. In detail, the network setting information may include information necessary for starting a communication connection with a predetermined network, in order for the ultrasound diagnosis apparatus 400 to be connected to the predetermined network to perform data exchange with an external apparatus. The network setting information will now be referred to as setting information.

The setting information may vary according to the types of networks to which the ultrasound diagnosis apparatus 400 is to be connected. For example, setting information that is applied to a Wi-Fi network may include any one or more of an extended service set identifier (ESSID), a service set identifier (SSID), an IP address for WiFi connection, access point (AP)-related information, and the like. Setting information that is applied to a wide area network (WAN) may include any one or more of service connection information, an IP set value for WAN connection, a network address translation (NAT) set value, and information about a networking method. The setting information may be stored for each external apparatus to which the ultrasound diagnosis apparatus 400 is connectable.

A case in which the ultrasound diagnosis apparatus 400 performs wireless communication with the wireless probe 410 or the external apparatus 430 by using a single communication module that follows a single communications standard will now be described.

For example, if the ultrasound diagnosis apparatus 400 is able to be connected to each of the wireless probe 410 and the external apparatus 430 via a Wi-Fi network, the ultrasound diagnosis apparatus 400 may store connection information used to facilitate a connection to an AP 411 of the wireless probe 410. The ultrasound diagnosis apparatus 400 may store connection information used to facilitate a connection to an AP 441 of the external apparatus 430. Network setting information for a first communication connection 450 between the ultrasound diagnosis apparatus 400 and the wireless probe 410 will now be referred to as first setting information, and network setting information for a second communication connection 460 between the ultrasound diagnosis apparatus 400 and the external apparatus 430 will now be referred to as second setting information. The AP 411 may be implemented using a hardware AP configured by hardware or a software AP configured by software.

Referring to FIG. 4, the ultrasound diagnosis apparatus 400 may store the first setting information for a communication connection with the wireless probe 410 via a Wi-Fi network in the controller 310 or the memory (not shown), and may be connected to the wireless probe 410 by using the first setting information. The ultrasound diagnosis apparatus 400 may also store the second setting information for a communication connection with the external apparatus 430 via a Wi-Fi network in the controller 310 or the memory (not shown), and may be connected to the external apparatus 430 by using the second setting information.

In detail, the controller 310 executes the first communication connection 450 by using the first setting information. When the first event occurs, the controller 310 automatically executes the second communication connection 460 by using the second setting information. In detail, when the first event occurs, the controller 310 may automatically terminate the first communication connection 450 and automatically start the second communication connection 460 so that the first communication connection 450 may be automatically changed to the second communication connection 460.

For example, when the external apparatus 430 includes the PACS database 434 included in the PACS, the communicator 330 of the ultrasound diagnosis apparatus 400 may receive first data from the wireless probe 410 via the first communication connection 450. When the first event occurs, the controller 310 of the ultrasound diagnosis apparatus 400 may automatically change a communication connection so as to terminate the first communication connection 450 and start the second communication connection 460, by using the second setting information. Under the control of the controller 310, the communicator 330 may transmit the first data to the PACS database 434 via the second communication connection 460. Then, the PACS database 434 may receive the first data via the second communication connection 460 and store the first data.

The structures and operations of the ultrasound diagnosis apparatuses 300 and 400 will now be described in detail with reference to FIGS. 5-12.

Figure 5:
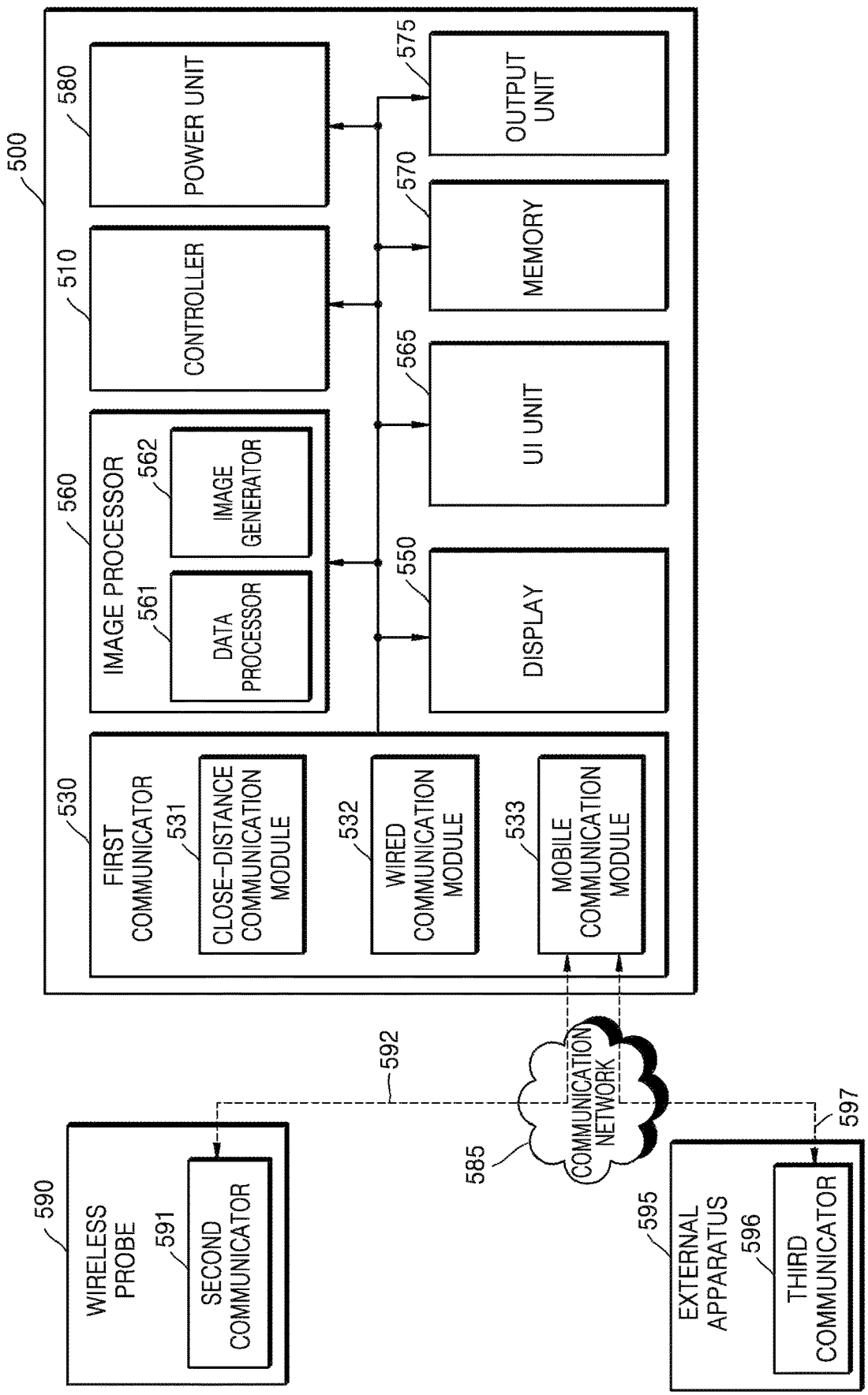
FIG. 5 is a block diagram of an ultrasound diagnosis apparatus, according to another exemplary embodiment.

FIG. 5 is a block diagram of an ultrasound diagnosis apparatus 500, according to another exemplary embodiment. The ultrasound diagnosis apparatus 500, a wireless probe 590, and an external apparatus 595 of FIG. 5 are respectively the same as the ultrasound diagnosis apparatus 300, the wireless probe 380, and the external apparatus 390 of FIG. 3, and thus repeated descriptions thereof will be omitted. The ultrasound diagnosis apparatus 500, the wireless probe 590, and the external apparatus 595 of FIG. 5 are respectively the same as the ultrasound diagnosis apparatus 400, the wireless probe 410, and the external apparatus 430 of FIG. 4, and thus repeated descriptions thereof will be omitted. A controller 510, a communicator 530, and a display 550 included in the ultrasound diagnosis apparatus 500 are respectively the same as the controller 310, the communicator 330, and the display 350 included in the ultrasound diagnosis apparatus 300 of FIG. 3, and thus repeated descriptions thereof will be omitted.

Referring to FIG. 4, the ultrasound diagnosis apparatus 500 includes the controller 510 and the communicator 530. The ultrasound diagnosis apparatus 500 may further include at least one selected from among the display 550, a UI unit (also referred to herein as a "user interface device") 565, a memory 570, an output unit (also referred to herein as an "output device") 575, and a power unit (also referred to herein as a "power component" and/or as a "power device") 580.

Referring to FIG. 4, the wireless probe 590 produces first data via scanning. A communicator 591 included in the wireless probe 590 may transmit the first data to the ultrasound diagnosis apparatus 500 via a communication network 585. Alternatively, the communicator 591 may transmit the first data to the ultrasound diagnosis apparatus 595 via the communication network 585.

The external apparatus 595 includes a communicator 596. The communicator 596 may transmit and/or receive data to or from the ultrasound diagnosis apparatus 500 or the wireless probe 590 via the communication network 585.

For convenience of explanation, the communicator 530 included in the ultrasound diagnosis apparatus 500 is hereinafter referred to as a first communicator 530, the communicator 591 included in the wireless probe 590 is hereinafter referred to as a second communicator 591, and the communicator 596 included in the external apparatus 595 is hereinafter referred to as a third communicator 596.

The first communicator 530 may include at least one communication module for transmitting and/or receiving data to or from the wireless probe 590, the external apparatus 595, and/or an externally-connected electronic apparatus (not shown) via a communication network. In detail, the first communicator 530 may include at least one selected from among a local area communication module 531, a wired communication module 532, and a mobile communication module 533.

The local area communication module 531 refers to a module which is configured for facilitating local area communication within a predetermined distance. Examples of local area communication techniques according to an exemplary embodiment may include, but are not limited to, Wi-Fi, Bluetooth, ZigBee, WFD, UWB, IrDA, BLE, and NFC. Accordingly, the local area communication module 531 may include at least one of communication modules that are respectively based on Wi-Fi, Bluetooth, ZigBee, WFD, UWB, IrDA, BLE, and NFC.

The wired communication module 532 refers to a module which is configured for facilitating communication using electric signals or optical signals. Examples of wired communication techniques according to an exemplary embodiment may include a pair cable, a coaxial cable, an optical fiber cable, and an Ethernet cable.

The mobile communication module 533 transmits and/or receives wireless signals to or from at least one selected from among a base station, an external terminal, and a server on a mobile communication network. The wireless signals may include any one or more of voice call signals, video call signals, and/or various types of data for transmission and reception of text/multimedia messages.

The first communicator 530 may transmit or receive predetermined data to or from an external electronic apparatus via any of various communication modules included in the communicator 530. The external electronic apparatus may include the wireless probe 590 and the external apparatus 595.

A case in which the communicator 530 exchanges data with the wireless probe 590 and/or the external apparatus 595 via the local area communication module 531, in detail, the communicator 530 exchanges data with the wireless probe 590 and/or the external apparatus 595 by using a single communication module (not shown) based on Wi-Fi or WFD communication technology (hereinafter, referred to as a Wi-Fi communication module) will now be illustrated.

The Wi-Fi communication module may be fixedly installed in the communicator 530 of the ultrasound diagnosis apparatus 500. The Wi-Fi communication module may be detachably installed in the ultrasound diagnosis apparatus 500, instead of being fixedly included in the ultrasound diagnosis apparatus 500. For example, the Wi-Fi communication module may be implemented by using a universal serial bus (USB), and thus may be installed in the ultrasound diagnosis apparatus 500 by being inserted into a USB port (not shown) included in the ultrasound diagnosis apparatus 500.

The display 550 may display an ultrasound image which corresponds to the first data received from the wireless probe 590. In detail, the display 550 may display any one or more of an ultrasound image produced using the first data, diagnosis data obtained by processing the first data, and data or an image produced based on the first data. The display 550 may display not only an ultrasound image but also any of various pieces of information processed by the ultrasound diagnosis apparatus 500, on a screen image via a graphical user interface (GUI).

The ultrasound diagnosis apparatus 500 may include two or more displays, according to one or more exemplary embodiments. In detail, the ultrasound diagnosis apparatus 500 may include any types of displays capable of visually displaying an image, such as, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a flat panel display (FPD), a 3D display, and/or a transparent display.

The image processor 560 may generate an ultrasound image by scan-converting ultrasound data included in the first data received from the wireless probe 590. In detail, the image processor 560 may include a data processor 561 and an image generator 562. The data processor 561 may pre-process the first data.

For example, when the first data includes ultrasound echo signals received by a transducer (not shown) of the wireless probe 590, the data processor 561 may receive and focus the ultrasound echo signals included in the first data in order to generate ultrasound data. Alternatively, the data processor 561 may perform amplification, noise removal, and/or the like on the ultrasound echo signals or ultrasound data included in the first data.

The ultrasound image may include not only a grayscale ultrasound image obtained by scanning an object in an amplitude (A) mode, a brightness (B) mode, and a motion (M) mode, but also a Doppler image showing a movement of an object via a Doppler effect. The Doppler image may include any one or more of a blood flow Doppler image showing flow of blood (also referred to as a color Doppler image), a tissue Doppler image showing a movement of tissue, and/or a spectral Doppler image showing a moving speed of an object as a waveform.

For example, when the image processor 560 tries to generate a B mode image, the data processor 561 extracts B mode components from the ultrasound data included in the first data and processes the B mode components. The image generator 562 may generate an ultrasound image which indicates signal intensities as brightness, based on the extracted B mode components.

In another example, when the image processor 560 tries to generate a Doppler image, the data processor 561 extracts Doppler components from the ultrasound data included in the first data. The image generator 562 may generate a Doppler image which indicates a movement of an object as colors or waveforms, based on the extracted Doppler components.

The data processor 561 of the image processor 560 may generate volume data by using the first data. The image generator 562 may generate a three-dimensional (3D) ultrasound image via volume rendering with respect to the volume data, and may also generate an elasticity image by imaging deformation of an object due to pressure. Furthermore, the image processor 560 may display any one or more of various pieces of additional information in an ultrasound image by using text and graphics. The generated ultrasound image may be stored in the memory 570.

The UI unit 565 refers to a device via which a user inputs data for controlling the ultrasound diagnosis apparatus 500. The UI unit 565 may include, but is not limited to, any one or more of hardware components, such as a keypad, a mouse, a touch pad, a touch screen, and a jog switch. The UI unit 565 may further include any of various other input units, including an electrocardiogram (ECG) measuring module, a respiration measuring module, a voice recognition sensor, a gesture recognition sensor, a fingerprint recognition sensor, an iris recognition sensor, a depth sensor, a distance sensor, and the like.

The UI unit 565 may produce and output a UI screen image for receiving a command or data from a user, and may receive a command or data from the user via the UI screen image. The user may recognize some information from the UI screen image displayed by the display 550, and may input a command or data via the UI unit 565.

For example, the UI unit 565 may include a touch pad. In detail, the UI unit 565 may include a touch pad (not shown) coupled with a display panel (not shown) included in the display 550. In this case, the UI screen image is displayed on the display panel. When a command is input via the UI screen image, the touch pad may sense the input operation and transmit information which corresponds to a result of the sensing to the controller 510. Then, the controller 510 interprets the information in order to thereby recognize and execute the command input by the user.

The memory 570 stores various pieces of information processed or generated by the ultrasound diagnosis apparatus 500. For example, the memory 570 may store medical data related to diagnosis of an object, such as ultrasound data and an ultrasound image, and may also store algorithms or programs which are to be executed in the ultrasound diagnosis apparatus 500.

The memory 570 may be any of various types of storage media, e.g., a flash memory, a hard disk drive, EEPROM, etc. The ultrasound diagnosis apparatus 500 may utilize a web storage and/or a cloud server which performs a storage function of the memory 570 online.

In detail, the memory 570 may store the first data which is transmitted by the communicator 530, the ultrasound image acquired based on the first data, and/or information acquired based on the first data.

In addition, the controller 510 may set information relating to a server or apparatuses which are to communicate with the ultrasound diagnosis apparatus 500 via the network 585. The memory 570 may store the set information about the server or apparatuses which are to communicate with the ultrasound diagnosis apparatus 500 via the network 585. In detail, the memory 570 may store first setting information for a first communication connection 592 and second setting information for a second communication connection 597. In detail, the memory 570 may store a method of setting a network with the server or apparatuses which are to communicate with the ultrasound diagnosis apparatus 500 via the network 585, and pieces of information relating to the network setting. The controller 510 may automatically start, stop, or restore a network connection with the server or apparatuses by using the information stored in the memory 570.

The output unit 575 is configured to output data that a user may recognize sensately, such as, by using his or her sense of vision, hearing, and/or touch, in addition to the display 550. Examples of the output unit 575 may include a speaker, a lamp, a vibrator, and the like.

The power unit 580 supplies power to each component included in the ultrasound diagnosis apparatus 500, under the control of the controller 510. In detail, the power unit 580 is charged, and may include a battery (not shown) which supplies power to each component included in the ultrasound diagnosis apparatus 500. The battery is charged. For example, the battery may be a rechargeable battery. Thus, when the battery is dead, the battery may be recharged by power supplied via a power line. The power unit 580 may also include a power line (not shown) configured to receive power from an external power source and to supply the received power to each component included in the ultrasound diagnosis apparatus 500.

Figure 6:
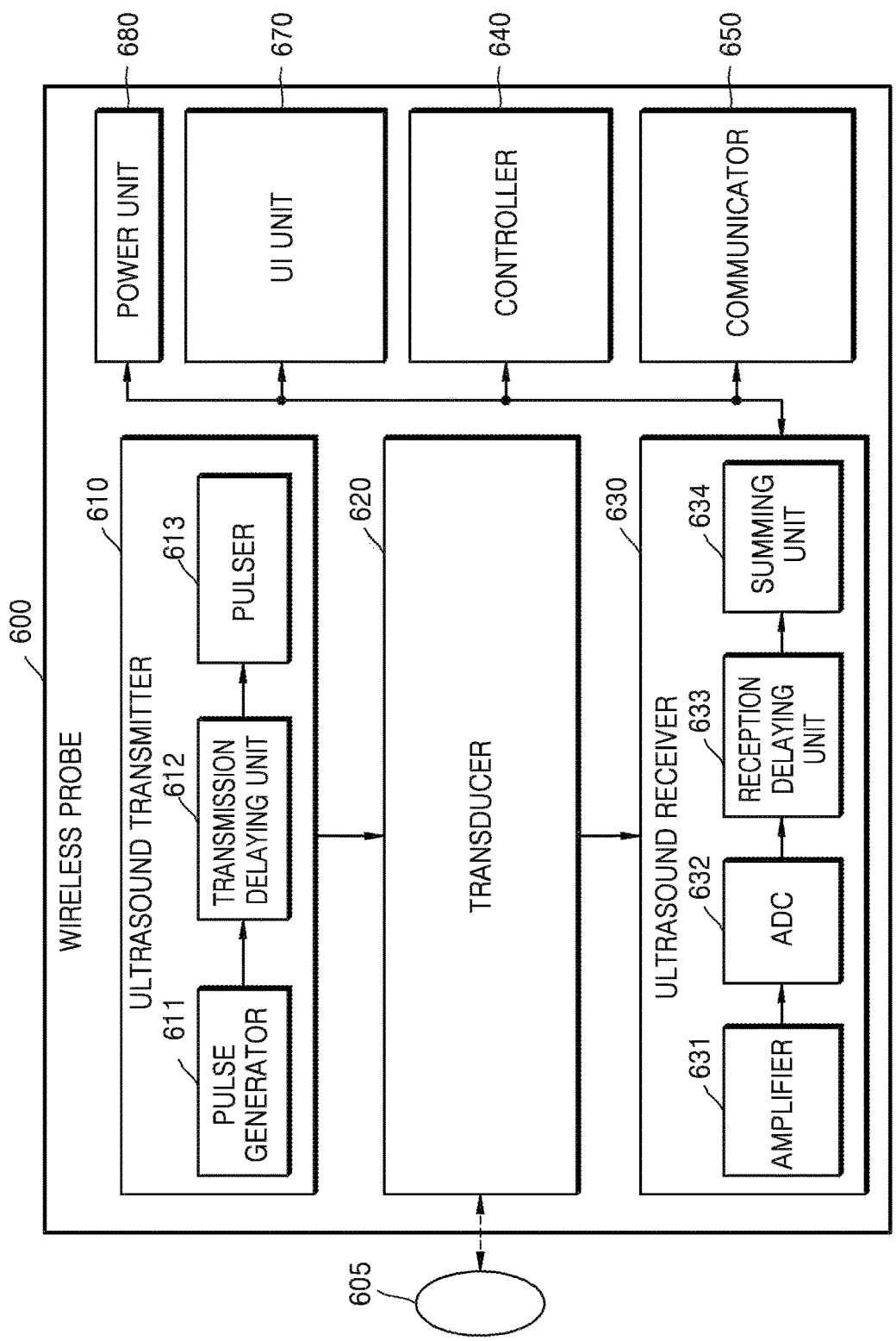
FIG. 6 is a block diagram of a wireless probe that is connected to an ultrasound diagnosis apparatus, according to an exemplary embodiment.

FIG. 6 is a block diagram of a wireless probe 600 that is connected to an ultrasound diagnosis apparatus, according to an exemplary embodiment.

Referring to FIG. 6, the wireless probe 600 scans an object 605 and acquires data, such as an ultrasound echo signal reflected from the object 605, for imaging an ultrasound image which corresponds to the scanned object 605. In detail, the wireless probe 600 transmits an ultrasound signal toward the object 605 and receives an ultrasound echo signal reflected by the object 605. The wireless probe 600 may generate ultrasound data which corresponds to the received ultrasound echo signal and wirelessly transmit the ultrasound data to the ultrasound diagnosis apparatus 500 of FIG. 5.

Referring to FIG. 6, the wireless probe 600 may include an ultrasound transmitter 610, a transducer 620, and an ultrasound receiver 630. The transducer 620 is an ultrasound scan device, and the wireless probe 600 generally includes a transducer array including a plurality of transducers. However, in FIG. 6, the transducer 620 corresponds to a plurality of transducers or to a transducer array included in the wireless probe 600.

The ultrasound transmitter 610 provides a driving signal to the transducer 620 so that the transducer 620 may generate a focused ultrasound signal which is to be transmitted to the object 605. In detail, the ultrasound transmitter 610 may include a pulse generator 611, a transmission delaying unit (also referred to herein as a "transmission delayer") 612, and a pulser 613.

The pulse generator 611 generates pulses for forming transmission ultrasound waves based on a predetermined pulse repetition frequency (PRF).

The transmission delaying unit 612 delays the pulses by delay times which correspond to determining transmission directionality. The pulses which have been delayed correspond to a plurality of piezoelectric vibrators (not shown) included in the transducer 620, respectively. Such a piezoelectric vibrator is also called as a piezo device. In detail, the transmission delaying unit 612 generates pulses for generating a focused ultrasound signal by focusing transmission ultrasound waves.

The pulser 613 applies a driving signal (or a driving pulse) to the transducer 620 based on timing that corresponds to each of the pulses which have been delayed.

The transducer 620 vibrates according to the pulses, which are applied electrical signals, generates ultrasound waves, which are acoustic energy, and transmits the ultrasound waves toward the object 605. The transducer 620 receives an ultrasound echo signal, which is an ultrasound signal reflected from the object 605.

The transducer 620 may include any one or more of an acoustic lens (not shown), a piezoelectric device (not shown), a matching layer (not shown), and a sound absorbing layer (not shown).

The piezoelectric device is formed of a piezoelectric effect element that converts an electrical signal into an acoustic signal and/or vice versa. Examples of the piezoelectric effect element may include, but are not limited to, any of a piezoelectric ceramic, a single crystal material, and a composite piezoelectric material that cause a piezoelectric effect. The composite piezoelectric material is formed by compounding a polymer material and any of the aforementioned materials. When the pulser 613 applies the pulses, which are generated electrical signals, to the piezoelectric device, an ultrasound signal may be generated within the piezoelectric device. Each pulse applied to the piezoelectric device is a voltage signal and thus has a predetermined voltage value.

The matching layer is disposed on a front surface of the piezoelectric device. The matching layer changes an acoustic impedance of the ultrasound waves generated by the piezoelectric device in stages, so that the acoustic impedance of the ultrasound waves is approximate to an acoustic impedance of the object 605. The front surface of the piezoelectric device may be a surface that is closest to the object 605 from among the surfaces of the piezoelectric device when ultrasound waves are applied to the object 605, and a rear surface thereof may be a surface opposite to the front surface. The matching layer is also called an acoustic matching layer.

The sound absorbing layer may support the piezoelectric device at the rear surface of the piezoelectric device, and absorb ultrasound waves that are transmitted toward the rear surface of the piezoelectric device and are thus not directly used in tests or diagnosis. The sound absorbing layer may include a plurality of electrodes which are configured for applying voltages to the piezoelectric device.

The acoustic lens is disposed on the front surface of the transducer 620, and focuses the ultrasound waves generated by the piezoelectric device. The acoustic lens may be formed of a material, such as silicon rubber, which has an acoustic impedance that is similar to that of the object 605.

The ultrasound receiver 630 focuses the ultrasound echo signal received from the transducer 620 in order to generate a focused ultrasound echo signal. In detail, the ultrasound receiver 630 focuses the ultrasound echo signal received from the transducer 620 in order to generate ultrasound data.

In detail, the ultrasound receiver 630 may include an amplifier 631, an analog-to-digital converter (ADC) 632, a reception delaying unit (also referred to herein as a "reception delayer") 633, and a summing unit (also referred to herein as a "summer") 634.

In detail, the amplifier 631 amplifies ultrasound echo signals in each channel, and the ADC 632 performs analog-to-digital conversion on the amplified ultrasound echo signals. The reception delaying unit 633 delays digital ultrasound echo signals output by the ADC 632 by delay times which correspond to determining reception directionality. Each channel is a respective channel for each element of the transducer 620.

The summing unit 634 generates ultrasound data by summing the ultrasound echo signals processed by the reception delaying unit 633. According to one or more exemplary embodiments, the ultrasound receiver 630 may not include the amplifier 631. In particular, if the sensitivity of the transducer 620 with respect to receiving the ultrasound echo signal is increased, or if the number of bits processed by the ADC 632 is increased, the amplifier 631 may be omitted.

The wireless probe 600 may further include at least one selected from a controller 640, a communicator 650, a UI unit 670, and a power unit 680.

The controller 640 controls all operations of the wireless probe 600. In detail, the controller 640 may control first data which includes at least one selected from among the ultrasound echo signal received from the transducer 620, the ultrasound data generated by the ultrasound receiver 630, an ultrasound image generated based on the ultrasound data, and information acquired using the ultrasound data, so that the first data is transmitted to the ultrasound diagnosis apparatus 500 and/or the external apparatus 595 via the communicator 650.

The communicator 650, the UI unit 670, and the power unit 680 are the same as the communicator 530, the UI unit 565, and the power unit 580 of FIG. 5, respectively, and thus detailed description thereof will be omitted.

An automatic communication connection switch between the first communication connection 592 and the second communication connection 597 under the control of the controller 510 of FIG. 5 will now be described in detail.

When the ultrasound diagnosis apparatus 500 communicates with the wireless probe 590 and the external apparatus 595 by using a single communication module included in the communicator 530, the ultrasound diagnosis apparatus 500 may not simultaneously exchange data with the wireless probe 590 and the external apparatus 595. For example, when the ultrasound diagnosis apparatus 500 communicates with the wireless probe 590 and the external apparatus 595 by using a Wi-Fi communication module (not shown) included in the local area communication module 531 of the communicator 530, the first communication connection 592 and the second communication connection 597 may not be maintained simultaneously. When one of the first communication connection 592 and the second communication connection 597 is activated, the other is stopped. In this case, the first communication connection 592 and the second communication connection 597 must be automatically switched with each other according to user's usage situations in order to perform data exchange according to the intention of a user. When the first event occurs, the ultrasound diagnosis apparatus 500 automatically switches the first communication connection 592 and the second communication connection 597 with each other to thereby achieve highly-efficient and highly-convenient data exchange.

In detail, while the first communication connection 592 is being maintained, the wireless probe 590 transmits the first data to the ultrasound diagnosis apparatus 500 in real time so that the ultrasound diagnosis apparatus 500 may process the first data and thus utilize related images and information. Subsequently, when a first event occurs, the first communication connection 592 is terminated and the second communication connection 597 is started, so that the ultrasound diagnosis apparatus 500 and the external apparatus 595 may perform necessary data exchange therebetween.

Thus, when a first event occurs, the controller 510 terminates the first communication connection 592 with the wireless probe 590 and starts the second communication connection 597 with the external apparatus 595.

In detail, the first event may occur based on an operational status of at least one selected from among the external apparatus 595, the wireless probe 590, and the ultrasound diagnosis apparatus 500. In detail, when the wireless probe 590 does not transmit or is determined not to be required to transmit the first data to the ultrasound diagnosis apparatus 500, or when the ultrasound diagnosis apparatus 500 is in an operational status in which a determination is made that it is not required to receive the first data, the first event may occur.

When ultrasound scanning starts, the ultrasound diagnosis apparatus 500 may activate the first communication connection 592 with the wireless probe 590 and thus receive the first data from the wireless probe 590. The display 550 may display an ultrasound image corresponding to the first data received from the wireless probe 590. An image that is generated based on the first data and represents an object scanned by the wireless probe 590 will now be referred to as a first ultrasound image. In detail, the first ultrasound image is an ultrasound image produced based on the first data, and may include any one or more of a B mode image, an M mode image, a Doppler image, or the like. Any type of information acquired based on the first data will now be referred to as first information. For example, any of various measured values that are used in diagnosis of an object may be acquired based on the first data. In detail, when an object is an embryo, the controller 510 may automatically acquire measured values of a biparential diameter (BPD), a head circumference (HC), a femur length (FL), a humeral length (HL), and a crow lump length (CRL), which represent the development characteristics of the embryo, from a first ultrasound image generated by using the first data. In the above-described example, the first information may include any of various measured values which are useful for diagnosing the object, such as, the measured values of the BPD, the HC, the FL, the HL, and the CRL.

When the first ultrasound image is set to be displayed, the controller 510 may control the first communication connection 592 to be activated. In detail, when display of the first ultrasound image is set according to a user input or preset by the controller, the controller 510 may control the first data to be transmitted from the second communicator 591 to the first communicator 530 via the first communication connection 592 with the wireless probe 590. The controller 510 may also control the image processor 560 to generate the first ultrasound image based on the first data and may control the display 550 to display the first ultrasound image. In particular, when a user sees the first ultrasound image displayed by the ultrasound diagnosis apparatus 500, the ultrasound diagnosis apparatus 500 is required to receive the first data from the wireless probe 590 via the first communication connection 592. Thus, in this case, the controller 510 may control the first communication connection 592 to be started and maintained.

The first event may occur in any case other than the case where the first ultrasound image is set to be displayed on the display 550. Thus, in any case other than the case where the first ultrasound image is set to be displayed, the controller 510 may recognize that the first event has occurred and thus may control the second communication connection 597 to be started or maintained. In detail, when an operation other than the operation of displaying the first ultrasound image is newly performed while the first communication connection 592 is being maintained, the controller 510 may terminate the first communication connection 592 and control the second communication connection 597 to start automatically.

The first event may also occur when the wireless probe 590 senses a cessation of a user manipulation. For example, the first event may occur when the wireless probe 590 stops scanning an object. When a user stops scanning for a moment, like when not manipulating the wireless probe 590, there is no new data that is acquired by wireless probe 590 by scanning an object, and thus a determination is made that the first data is not required to be transmitted. Therefore, in this case, the controller 510 may terminate the first communication connection 592 and control the second communication connection 597 to start automatically, so that necessary data exchange between the ultrasound diagnosis apparatus 500 and the external apparatus 595 may be performed.

The first event may also occur when the current display of the first ultrasound image on the display 550 is terminated. In detail, while the display 550 is displaying the first ultrasound image, a user may request termination of the display of the first ultrasound image via the UI unit 565. When the user request is received, the controller 510 recognizes that the first event has occurred, and terminates the first communication connection 592 and starts the second communication connection 597.

The first event may also occur when a user manipulation with respect to the ultrasound diagnosis apparatus 500 is not sensed for a predetermined period of time. In detail, the first event may occur when the ultrasound diagnosis apparatus 500 enters a standby mode. In detail, like when the ultrasound diagnosis apparatus 500 enters a standby mode, when a user does not manipulate the ultrasound diagnosis apparatus 500 for a predetermined period of time or longer, it may be determined that the user does not use the ultrasound diagnosis apparatus 500. In particular, if the user does not use the ultrasound diagnosis apparatus 500 even when the ultrasound diagnosis apparatus 500 receives the first data, an image or information acquired using the first data is determined to be not required to be processed or displayed, and thus the controller 510 may terminate the first communication connection 592 and start the second communication connection 597.

In detail, while the first communication connection 592 is being maintained, the wireless probe 590 transmits the first data to the first communicator 530 of the ultrasound diagnosis apparatus 500 via the second communicator 591 in real time. When the first data is transmitted to the ultrasound diagnosis apparatus 500 in real time, the ultrasound diagnosis apparatus 500 may display at least one selected from among the first ultrasound image corresponding to the first data and information acquired based on the first data in real time.

The first event may occur when the display 550 displays a screen image which does not include the first ultrasound image corresponding to the first data. In detail, the first event may occur when the display 550 displays an image or information which is unrelated to the first data, or when the UI unit 565 is requested to display the image or information which is unrelated to the first data.

The first event may also occur when the display 550 displays a still image. In detail, when the ultrasound diagnosis apparatus 500 is requested by a user via the UI unit 565 to stop displaying a screen image while receiving the first data in real time and displaying the first ultrasound image in real time, the first event may occur in response to a reception of the screen image display stop request from the user. When the screen stoppage is requested, the ultrasound diagnosis apparatus 500 is determined to be not required to display a first ultrasound image that is updated in real time in correspondence to first data that is updated and transmitted in real time, and thus is not required to receive the first data that is updated in real time. Therefore, the controller 510 may terminate the first communication connection 592 and start the second communication connection 597.

When the ultrasound diagnosis apparatus 500 receives the first data in real time, acquires first information in real time by using the first data, and displays the first information, the first event may occur when the display of the first information is stopped.

As described above, when display of the first ultrasound image is requested, the controller 510 may start or maintain the first communication connection 592. When display of the first ultrasound image is not requested, the controller 510 may start or maintain the second communication connection 597.

In detail, when the ultrasound diagnosis apparatus 500 does not store, process, or display an image or information based on the first data received from the wireless probe 590, the ultrasound diagnosis apparatus 500 is determined not to be required to receive the first data from the wireless probe 590. Thus, when the ultrasound diagnosis apparatus 500 does not process, or display the image or information based on the first data, the controller 510 of the ultrasound diagnosis apparatus 500 may recognize that the first event has occurred, and thus may terminate the first communication connection 592 and start the second communication connection 597. When the second communication connection 597 starts, the ultrasound diagnosis apparatus 500 may exchange data with the external apparatus 595 via the second communication connection 597.

The first event may also occur when an ultrasonic diagnosis being performed on an object terminates. In detail, when the ultrasonic diagnosis being performed on an object terminates, further scanning is not needed, and the wireless probe 590 is no longer required to transmit the first data to the ultrasound diagnosis apparatus 500. Thus, when the ultrasonic diagnosis being performed on an object terminates, the controller 510 may recognize that the first event has occurred, and may accordingly terminate the first communication connection 592 and start the second communication connection 597.

When the ultrasonic diagnosis being performed on an object terminates and the second communication connection 597 starts, the controller 510 may receive an MWL from the external apparatus 595 via the second communication connection 597. The MWL may include information regarding diagnosis of patients. In detail, the MWL may include at least one selected from among a list of patients who are to undergo an ultrasonic diagnosis, information about the patients, and concrete schedules for diagnoses of the patients. The receiving of the MWL may be automatically performed when the ultrasound diagnosis apparatus 500 is requested via the UI unit 565 to display the MWL or when the ultrasonic diagnosis is terminated. Then, the display 550 may display the received MWL. Thereafter, a user may select a patient from the MWL or input new patient information not included in the MWL in order to thereby start a new ultrasonic diagnosis. When the new ultrasonic diagnosis starts, the controller 510 may terminate the second communication connection 597 and restore the first communication connection 592. Accordingly, the wireless probe 590 may transmit the first data acquired by scanning a new patient to the ultrasound diagnosis apparatus 500.

Therefore, when the receiving of the MWL is completed, the controller 510 may automatically terminate the second communication connection 597 and restore the first communication connection 592.

When the external apparatus 595 is a server included in a hospital, the MWL may be received from the server via the second communication connection 597 according to the DICOM standard. The DICOM standard is a standard which relates to compressing medical images and related information, thus increasing the efficiency of managing and storing data that is exchanged.

The operation in which the ultrasound diagnosis apparatus 500 receives the MWL according to the DICOM standard will now be described in detail.

In detail, when the ultrasound diagnosis apparatus 500 is requested by a user via the UI unit 565 to display the MWL, the controller 510 may recognize that the first event has occurred. At this time, when the first communication connection 592 is maintained, the controller 510 may terminate the first communication connection 592 and start the second communication connection 597. Conversely, when the first communication connection 592 is not maintained, the controller 510 may start or maintain the second communication connection 597. When the second communication connection 597 is completed, the controller 510 requests the external apparatus 595 to transmit the MWL, via a DICOM worklist query. Accordingly, the external apparatus 595 transmits the MWL to the first communicator 530 of the ultrasound diagnosis apparatus 500 via the third communicator 596. When the reception of the MWL is completed, the controller 510 may terminate the second communication connection 597. Furthermore, when the reception of the MWL is completed, the controller 510 may terminate the second communication connection 597 and automatically start the first communication connection 592.

When the MWL is received by the ultrasound diagnosis apparatus 500, the controller 510 may control a screen image which includes the MWL to be displayed so that a user may select a suitable ultrasonography which corresponds to a work item included in the MWL. The user may select a work item from the displayed MWL so that a suitable ultrasonography is conducted.

When the work item is selected from the MWL, the controller 510 may terminate the second communication connection 597 and control the first communication connection 592 to automatically start.

Moreover, when the MWL is displayed but a work item is not yet selected from the displayed MWL, the controller 510 may still terminate the second communication connection 597 and control the first communication connection 592 to start, in order to prepare for ultrasound scanning.

While the ultrasound diagnosis apparatus 500 is exchanging data with at least one selected from the wireless probe 590 and the external apparatus 595, the controller 510 may control a UI screen image which includes information indicating a data exchange situation to be displayed. In detail, the UI screen image may include information which includes the type and size of data that is exchanged and the amount or percentage of data that has been currently transmitted.

When the ultrasound diagnosis apparatus 500 continues data exchange with at least one selected from among the wireless probe 590 and the external apparatus 595 for a predetermined period of time or longer, the controller 510 may control the data exchange to be conducted in a background environment. The background environment denotes an operational environment that prevents a screen image which represents an execution of a certain operation from being displayed. In detail, when the ultrasound diagnosis apparatus 500 continues data exchange with at least one selected from among the wireless probe 590 and the external apparatus 595 for a predetermined period of time or longer, the controller 510 terminates outputting of a UI screen image which shows execution and progress situations of the data exchange, and controls the data exchange to be continued without outputting the UI screen image. Moreover, after the data exchange is performed in the background environment, the controller 510 may control a UI screen image which indicates a completion of the data exchange to be output when the data exchange is completed.

The first event may occur based on a user input that is generated via the wireless probe 590. The occurrence of the first event according to the user input which is received via the wireless probe 590 will now be described in detail with reference to FIGS. 7A and 7B.

Figure 7A:
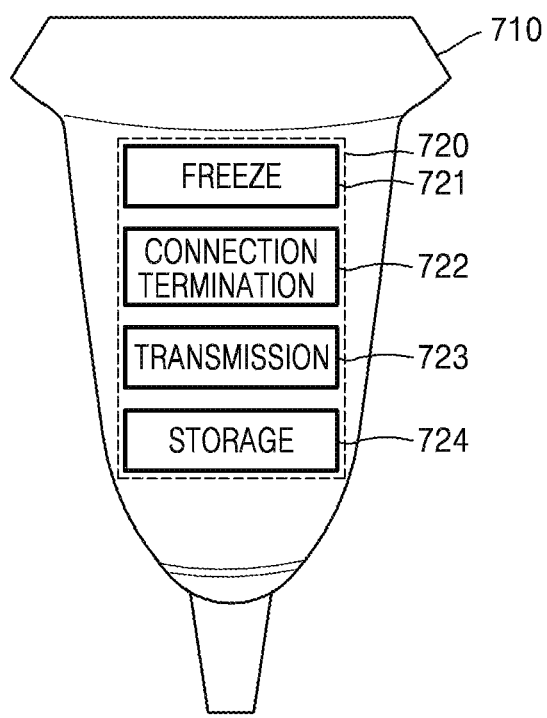
FIGS. 7A and 7B illustrate wireless probes which are connected to an ultrasound diagnosis apparatus, according to an exemplary embodiment.
Figure 7B:
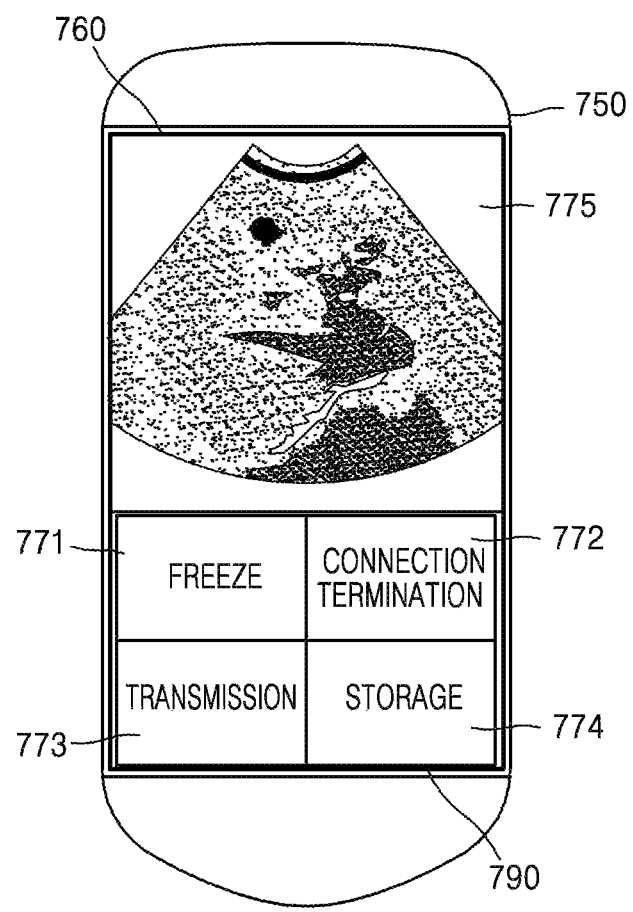

FIGS. 7A and 7B illustrate wireless probes 710 and 750 which are connected to an ultrasound diagnosis apparatus, according to an exemplary embodiment. The wireless probes 710 and 750 illustrated in FIGS. 7A and 7B have different shapes.

The wireless probe 710 of FIG. 7A is the same as the wireless probe 110 of FIG. 1, and thus a repeated description thereof will be omitted. The wireless probe 750 of FIG. 7B is the same as the wireless probe 210 of FIG. 2, and thus a repeated description thereof will be omitted. Each of the wireless probes 710 and 750 of FIGS. 7A and 7B is the same as the wireless probe 590 of FIG. 5, and thus a repeated description thereof will be omitted.

Referring to FIG. 7A, the wireless probe 710 includes a UI unit 720 which includes at least one selected from among at least one hard key, a soft key, a track boll, and a jog switch. Since the UI unit 720 corresponds to the UI unit 565 of FIG. 5, a repeated description thereof will be omitted. FIG. 7A illustrates a case where the UI unit 720 includes four hard keys.

The UI unit 720 may include a FREEZE key 721 configured for requesting that ultrasound scanning be paused, a connection termination key 722 configured for requesting that communication connection between the wireless probe 710 and the ultrasound diagnosis apparatus 500 be terminated, a transmission key 723 configured for requesting that first data acquired via the ultrasound scanning be transmitted to the external apparatus 595, and a storage key 724 configured for requesting that the first data be stored. The transmission key 723 may be a key configured for requesting that pre-set transmission of the first data to the external apparatus 595 be performed. The storage key 724 may be a key configured for requesting that the ultrasound diagnosis apparatus 500 store the first data. In this case, when the storage key 724 is selected, the first data may be transmitted to the ultrasound diagnosis apparatus 500. When the wireless probe 710 includes an internal memory (not shown), the storage key 724 may be a key configured for requesting that the internal memory store the first data.

The wireless probe 710 may include a controller (not shown). When one of the keys included in the UI unit 720 is selected and pressed, the UI unit 720 transmits a user input signal corresponding to the pressed key to the controller (not shown) of the wireless probe 710. The controller may receive the user input signal via the UI unit 720 and perform an operation which corresponds to the received user input signal.

In detail, a first event may occur in response to a request to terminate transmission of data received by the wireless probe 710, which is received via the wireless probe 710. In detail, when the connection termination key 722 of the UI unit 720 is selected, the controller of the wireless probe 710 recognizes that the first event has occurred, and informs the ultrasound diagnosis apparatus 500 of the occurrence of the first event. Then, the controller 510 of the ultrasound diagnosis apparatus 500 may terminate the first communication connection 592 and control the second communication connection 597 to start.

The first event may also occur in response to a reception of a request to transmit data to the external apparatus 595, which is received via the wireless probe 595. In detail, when the transmission key 723 of the UI unit 720 is selected, the controller of the wireless probe 710 recognizes that the first event has occurred, and informs the ultrasound diagnosis apparatus 500 of the occurrence of the first event. Then, the controller 510 of the ultrasound diagnosis apparatus 500 may terminate the first communication connection 592 and control the second communication connection 597 to start.

Furthermore, when the transmission key 723 is selected, the controller of the wireless probe 710 may terminate the first communication connection 592 and directly start a communication connection to the external apparatus 595. When the communication connection between the external apparatus 595 and the wireless probe 590 is completed, the wireless probe 590 may directly transmit the first data to the external apparatus 595.

The first event may also occur in response to a scanning stop request that is received via the wireless probe 710. In detail, when the FREEZE key 721 of the UI unit 720 is selected, the controller of the wireless probe 710 recognizes that the first event has occurred, and informs the ultrasound diagnosis apparatus 500 of the occurrence of the first event. Then, the controller 510 of the ultrasound diagnosis apparatus 500 may terminate the first communication connection 592 and control the second communication connection 597 to start.

The wireless probe 750 of FIG. 7B may be a smart device which is capable of ultrasound scanning. The wireless probe 750 may include a touch screen 760, and the touch screen 760 corresponds to the UI unit 720 of FIG. 7A. The touch screen 760 is the same as the display 550 and the UI unit 565 of FIG. 5, and thus a detailed description thereof will be omitted.

In detail, the touch screen 760 may output a UI screen image and receive a user input via the UI screen image. In detail, the touch screen 760 includes a touch pad (not shown) coupled with a display panel (not shown), and outputs a UI screen image to the display panel. When a command is input via the UI screen image, the touch pad may sense the input operation and recognize the command input by the user.

The touch screen 760 may output a UI screen image, the UI screen image including an ultrasound image 775 acquired based on data acquired by ultrasound scanning and at least one selected from menu keys, namely, a FREEZE key 771, a connection termination key 772, a transmission key 773, and a storage key 774, for a user input.

When one of the FREEZE key 771, the connection termination key 772, the transmission key 773, and the storage key 774 is selected and pressed, a user input corresponding to the pressed menu key is transmitted to a controller (not shown) of the wireless probe 750. The controller may receive the user input made via the touch screen 760 and perform an operation which corresponds to the received user input.

The FREEZE key 771, the connection end key 772, the transmission key 773, and the storage key 774 of FIG. 7B are respectively the same as the FREEZE key 721, the connection end key 722, the transmission key 723, and the storage key 724 of FIG. 7A, and thus detailed descriptions thereof will be omitted.

The first event may also occur based on a user input that is generated via the ultrasound diagnosis apparatus 500. The occurrence of the first event according to the user input made via the ultrasound diagnosis apparatus 500 will now be described in detail with reference to FIGS. 8A and 8B.

Figure 8A:
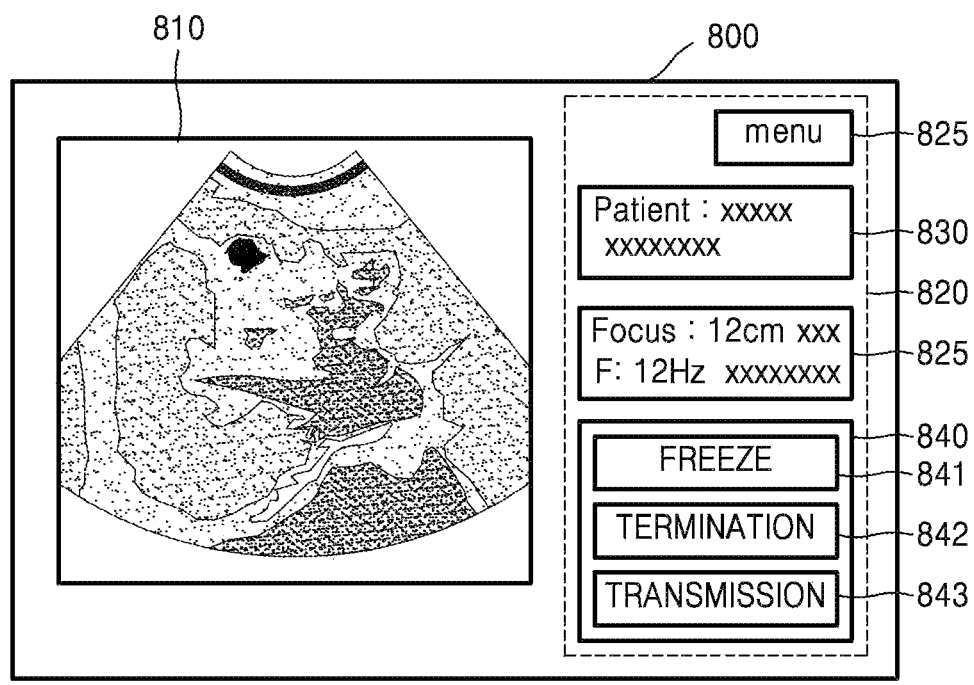
FIGS. 8A and 8B illustrate screen images displayed on exemplary embodiments of an ultrasound diagnosis apparatus.
Figure 8B:
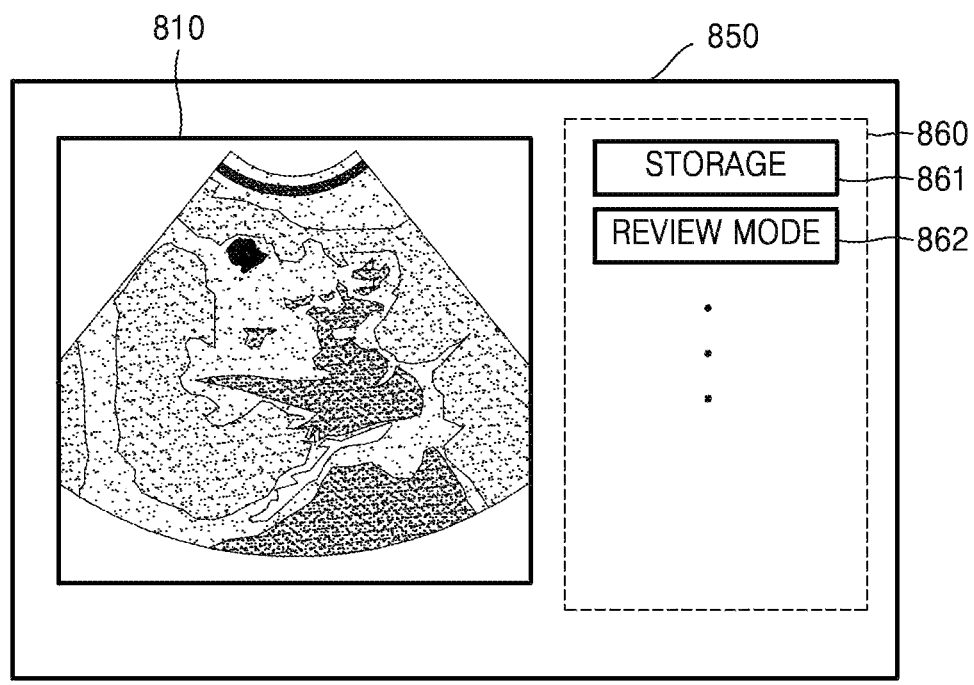

FIGS. 8A and 8B illustrate screen images displayed on exemplary embodiments of an ultrasound diagnosis apparatus. FIG. 8A illustrates a UI screen image 800 displayed on the display 550. FIG. 8B illustrates a UI screen image 850 displayed on the display 550.

Referring to FIG. 8A, the UI screen image 800 may include at least one selected from among a first ultrasound image 810, first information (not shown), a menu key 825 requesting that a menu screen image which is useful for performing an ultrasound diagnosis be output, patient-related information 830, information 825 about an ultrasound scanning environment, and at least one menu key 840 which relates to scanning or data exchange, based on the first data transmitted by the wireless probe 590.

The at least one menu key 840 may include at least one selected from among a FREEZE key 841, a termination key 842 configured for requesting that the first communication connection 592 to the wireless probe 590 or an ultrasound diagnosis be terminated, and a transmission key 843 configured for requesting that data exchange with the external apparatus 595 be performed.

In detail, the first event may occur in response to a scanning pause request that is received via the UI unit 565. In detail, when the FREEZE key 841 is selected and pressed via the UI unit 565, the controller 510 may recognize that the first event has occurred, and may terminate the first communication connection 592 and control the second communication connection 597 to start.

The first event may also occur in response to a selection of the termination key 842 via the UI unit 565. In detail, when the termination key 842 is selected and pressed via the UI unit 565, the controller 510 may recognize that the first event has occurred, and may terminate the first communication connection 592 and control the second communication connection 597 to start.

The first event may also occur in response to a selection of the transmission key 843 via the UI unit 565. In detail, when the transmission key 843 is selected and pressed via the UI unit 565, the controller 510 may recognize that the first event has occurred, and may terminate the first communication connection 592 and control the second communication connection 597 to start.

Referring to FIG. 8B, the UI screen 850 may include at least one menu key 860 configured for processing the first data transmitted by the wireless probe 590. In detail, the menu key 860 may include a storage key 861 configured for requesting that the first data be stored, a review mode key 862 configured requesting that a first ultrasound image which corresponds to previously-stored first data be displayed, and a key (not shown) configured for requesting that an ultrasound image according to a specific mode be generated.

In detail, the first event may occur when the memory 570 stores first data or an ultrasound image which corresponds to the first data is generated under the control of the controller 510. In detail, when a reception of first data is completed, the ultrasound diagnosis apparatus 500 may generate an ultrasound image of a part of an object which is to be diagnosed, and a determination may be made that it is not required to receive additional data from the wireless probe 590. Thus, when the reception of the first data is completed, the controller 510 may recognize that the first event has occurred, and accordingly terminate the first communication connection 592 and control the second communication connection 597 to start. When generation of the ultrasound image of the part which is to be diagnosed is completed, a user such as a medical doctor is able to diagnose the object via the generated ultrasound image. Thus, the wireless probe 590 is determined not to be required to further transmit first data. Thus, when generation of the first ultrasound image, namely, the ultrasound image of the part which is to be diagnosed, is completed, the controller 510 may recognize that the first event has occurred, and accordingly terminate the first communication connection 592 and control the second communication connection 597 to start.

When the memory 570 stores previously received first data, the first event may also occur in response to a request for a review mode. In detail, when the review mode key 862 is selected via the UI unit 565, the controller 510 may recognize that the first event has occurred, and may terminate the first communication connection 592 and control the second communication connection 597 to start. In the review mode, an ultrasound image generated based on the first data previously-stored in the memory 570 is displayed. Accordingly, when the review mode is requested, the ultrasound diagnosis apparatus 500 is determined not to be required to receive new data from the wireless probe 590. Thus, the controller 510 may terminate the first communication connection 592 and control the second communication connection 597 to start, in the review mode.

As described above with respect to other exemplary embodiments, when a first event which corresponds to a circumstance in which data exchange between the wireless probe 590 and the ultrasound diagnosis apparatus 500 is no longer required occurs, the controller 510 automatically changes communication connection in response to the occurrence of the first event so that the first communication connection 592 terminates and the second communication connection 597 starts. The ultrasound diagnosis apparatus 500 may exchange data with the external apparatus 595 via the second communication connection 597. Therefore, when the ultrasound diagnosis apparatus 500 is required to exchange data with a plurality of apparatuses by using a single communication module that follows a single communication standard, the ultrasound diagnosis apparatus 500 quickly and conveniently changes communication connection while affecting the data exchange operation as little as possible, thereby increasing user convenience and the operational efficiency of the ultrasound diagnosis apparatus 500.

Figure 9:
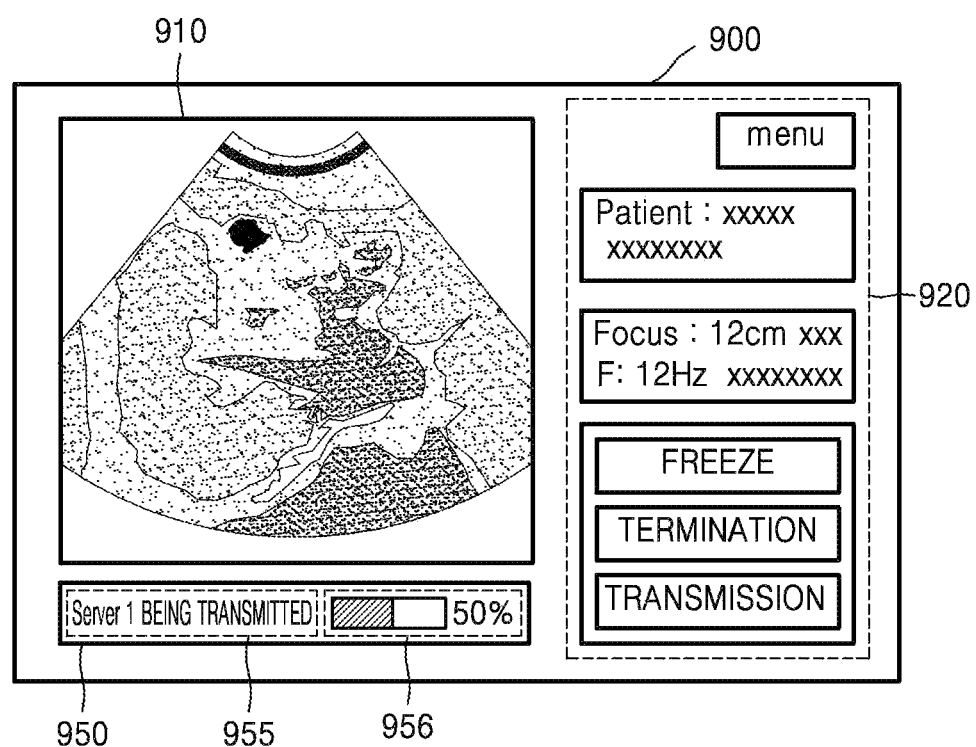
FIG. 9 illustrates a user interface (UI) screen image displayed on exemplary embodiments of an ultrasound diagnosis apparatus.

FIG. 9 illustrates a screen image displayed on exemplary embodiments of an ultrasound diagnosis apparatus. For example, FIG. 9 illustrates a UI screen image 900 displayed on the display 550. All components of the UI screen image 900 except for a menu 950 which includes information relating to data exchange situations are the same as the UI screen image 800 of FIG. 8A, and thus repeated descriptions thereof will be omitted.

When the second communication connection 597 starts, the controller 510 may transmit, to the external apparatus 595, first data and second data, the second data including at least one selected from among first ultrasound images which correspond to the first data. The second data may also include the above-described first information. In detail, when the second communication connection 597 starts, the controller 510 transmits information acquired by scanning an object to the external apparatus 595 so that the external apparatus 595 may utilize the information.

The controller 510 may control the UI screen image 900, including the menu 950 which relates to data exchange situations, so that the UI screen image 900 may be displayed.

Referring to FIG. 9, the menu 950 may include at least one selected from information 955 which relates to an apparatus connected via the second communication connection 597 and information 956 which relates to a percentage of transmitted data and/or a capacity of data that is transmitted. Accordingly, a user may easily ascertain situations of data exchange with a current external apparatus 595 from the menu 950. When the ultrasound diagnosis apparatus 500 continues data exchange with the external apparatus 595 for a predetermined period of time or longer, the controller 510 may control the data exchange to be conducted in a background environment so that the menu 950 may not be output.

The menu 950 may further include information that indicates an apparatus which is to exchange data with the ultrasound diagnosis apparatus 500 via the network 585 (for example, a wireless probe or an external apparatus), a network used for data exchange, and/or progress situations of data exchange. For example, the menu 950 may further include information which relates to an apparatus that is being connected, information which relates to a network that is being used, a point of time when communication connection starts, and information which relates to the type or the like of data that is exchanged.

The memory 570 may store termination information including at least one selected from among status information of communication with the wireless probe 590 at a first point of time when the first communication connection 592 terminates and information which relates to received data. In detail, when the first communication connection 592 is terminated due to occurrence of the first event and then the first communication connection 592 is restored at a subsequent point of time, data exchange should resume without duplication or omission of data transmission after data exchange performed via the previous first communication connection 592. Accordingly, the controller 510 may control information which indicates the status of the data exchange performed when the first communication connection 592 terminates so that the information is stored in the memory 570. In detail, when the first communication connection 592 has been terminated, information representing the location of transmission-completed data, information which relates to a point in time when the first communication connection 592 terminates, and information representing the location of not-yet transmitted data may be stored in the memory 570.

When the communication connection is changed and then the first communication connection 592 is restored so as to resume data exchange between the wireless probe 590 and the ultrasound diagnosis apparatus 500, the controller 510 may control data to be received subsequent to previously-transmitted data, based on the termination information stored in the memory 570. In detail, when the second communication connection 597 terminates and then the first communication connection 592 is restored, the controller 510 may resume data exchange by using the termination information stored in the memory 570, without duplication or omission of data transmission.

When a second event occurs after communication connection is changed as a result of the occurrence of the first event, the controller 510 may terminate the second communication connection 597 and control the first communication connection 592 to be restored. The second event may occur based on an operational status of at least one selected from the wireless probe 590, the external apparatus 595, and the ultrasound diagnosis apparatus 500.

In detail, the second event may occur when further data exchange between the ultrasound diagnosis apparatus 500 and the wireless probe 590 becomes necessary. Thus, when the second event occurs, the controller 510 may automatically terminate the second communication connection 597 and control the first communication connection 592 to be automatically restored.

In particular, when a scanning stop request previously received by at least one selected from the wireless probe 590 and the ultrasound diagnosis apparatus 500 is canceled, the controller 510 may terminate the second communication connection 597 and restore the first communication connection 592. In detail, when the FREEZE key 721 or 771 of the wireless probe 710 or 750 of FIG. 7A or FIG. 7B is pressed and subsequently is re-pressed to release a FREEZE operation, scanning of an object is resumed. Accordingly, first data is generated, and the newly generated first data is required to be transmitted from the wireless probe 590 to the ultrasound diagnosis apparatus 500. Thus, the controller 510 terminates the second communication connection 597 and restores the first communication connection 592 so that the first data may be received via the first communication connection 592.

As described above with reference to FIG. 8A, when the FREEZE key 841 is selected via the UI unit 565, the controller 510 may terminate the second communication connection 597 and restore the first communication connection 592.

Even when at least one of the wireless probe 590 and the ultrasound diagnosis apparatus 500 has not received a scanning stop request, if a request to scan an object is received by at least one of the wireless probe 590 and the ultrasound diagnosis apparatus 500, the controller 510 may terminate the second communication connection 597 and restore the first communication connection 592.

The second event may also occur when a determination is made that a data exchange between the ultrasound diagnosis apparatus 500 and the wireless probe 590 is no longer necessary. For example, when exchange of the second data is completed, the controller 510 may determine that the second event has occurred, and thus terminate the second communication connection 597 and control the first communication connection 592 to be restored. When data exchange with the external apparatus 595 is completed, communication connection with the external apparatus 595 no longer needs to be maintained. Thus, the controller 510 may change the communication connection in order to prepare for next ultrasound scanning.

A user may set the first event and/or the second event. In detail, the UI unit 565 may output a UI screen image (not shown) for setting at least one selected from the first event and the second event. The user may set at least one selected from the first event and the second event via the output UI screen image. When the set first event or the set second event is stored in the memory 570 and an event which matches with the stored first event or the stored second event occurs, the controller 510 may perform the aforementioned communication connection change.

Figure 10:
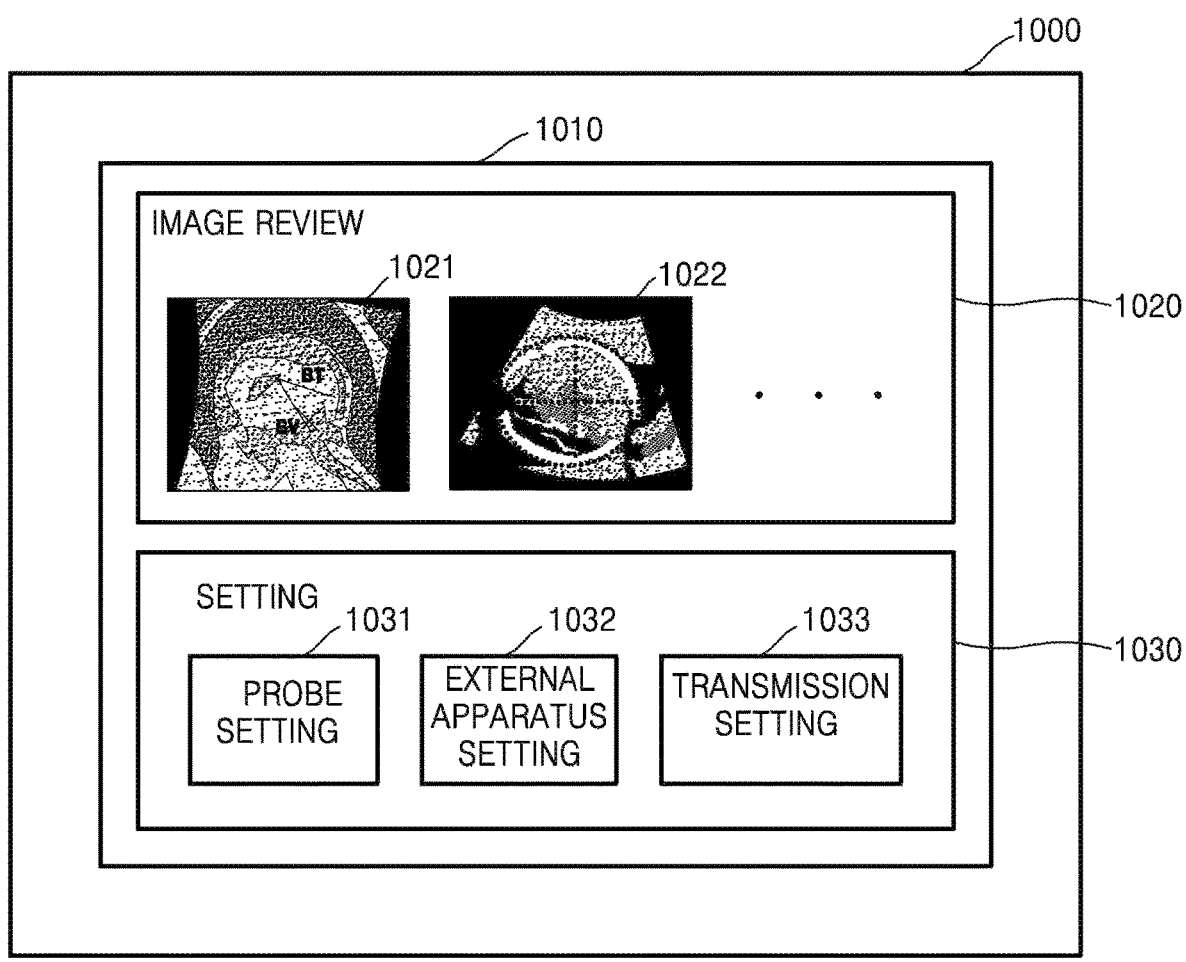
FIG. 10 illustrates a UI screen image displayed on exemplary embodiments of an ultrasound diagnosis apparatus.

FIG. 10 illustrates a UI screen image 1000 which may be displayed on exemplary embodiments of an ultrasound diagnosis apparatus.

Figure 11A:
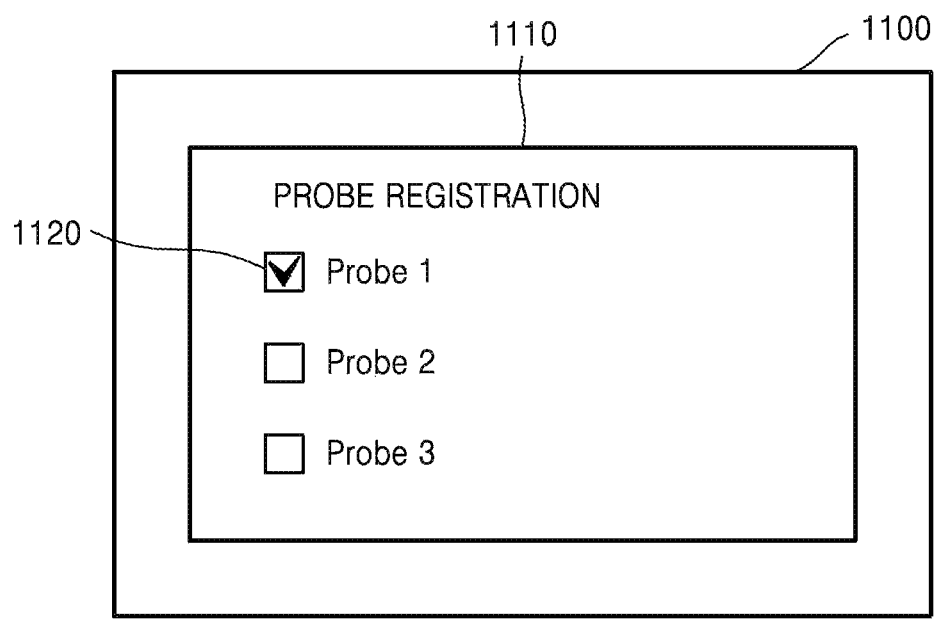
FIGS. 11A and 11B illustrate UI screen images displayed on exemplary embodiments of an ultrasound diagnosis apparatus.
Figure 11B:
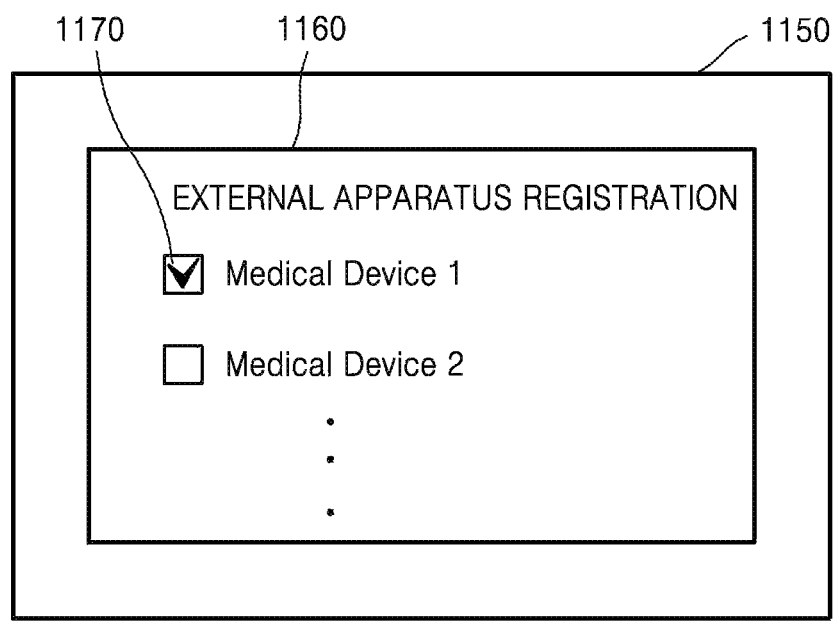

FIGS. 11A and 11B illustrate UI screen images 1100 and 1150 which may be displayed on exemplary embodiments of an ultrasound diagnosis apparatus.

Figure 12:
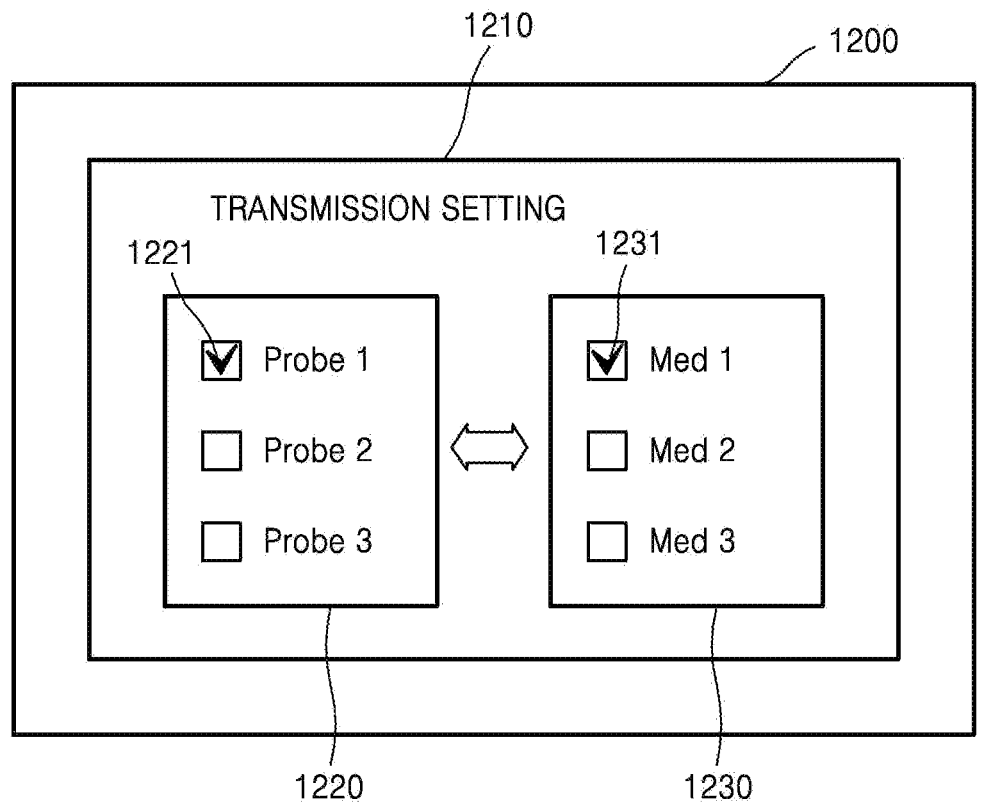
FIG. 12 illustrates a UI screen image displayed on exemplary embodiments of an ultrasound diagnosis apparatus.

FIG. 12 illustrates a UI screen image 1200 which may be displayed on exemplary embodiments of an ultrasound diagnosis apparatus.

Initial setting related with data exchange of the ultrasound diagnosis apparatus 500 will now be described in detail with reference to FIGS. 10, 11A, 11B, and 12.

Referring to FIG. 10, the UI unit 565 may produce the UI screen image 1000 including a menu window 1010, the menu window 1010 including at least one selected from a probe setting menu 1031 for registering and/or setting the wireless probe 590 which is connected to the ultrasound diagnosis apparatus 500, an external apparatus setting menu 1032 for registering and/or setting the external apparatus 595 which is connected to the ultrasound diagnosis apparatus 500, a transmission setting menu 1033 for setting transmission parameters with respect to data exchange, and a menu 1020 for executing a review mode. The display 550 displays the UI screen image 1000.

The menu 1020 may be displayed on the UI screen image 1000 when a review mode is requested, and may include a plurality of items 1021 and 1022 including pre-stored images. When a user selects one of the items 1021 and 1022, the controller 510 reproduces an image included in the selected item.

The probe setting menu 1031 includes menu items which relate to registering or unregistering wireless probes which are connectable to the ultrasound diagnosis apparatus 500 and/or menu items which relate to setting parameters for wireless probes by default.

When the probe setting menu 1031 is selected, the UI screen image 1100 of FIG. 11A may be output and displayed.

Referring to FIG. 11A, the UI screen image 1100 may include a list 1110 of probes which are configured for communicating with the ultrasound diagnosis apparatus 500. In detail, a case in which the ultrasound diagnosis apparatus 500 communicates with a wireless probe by using a Wi-Fi communication module based on Wi-Fi or WFD communication technology and the wireless probe includes an AP as described above with reference to FIG. 4 is illustrated. The local area communication module 531 performs an AP search to search for connectable wireless probes Probe 1, Probe 2, and Probe 3. Then, the controller 510 may control the UI screen image 1100 including the list 1110 of the wireless probes Probe 1, Probe 2, and Probe 3 that are connectable wireless probes found by the local area communication module 531 so that the UI screen image 1100 may be output. Accordingly, the display 550 may display the UI screen image 1100 which includes the list 1110 of the connectable wireless probes.

A user may select a wireless probe which is configured to be connected by default to the ultrasound diagnosis apparatus 500, by using the displayed UI screen image 1100. FIG. 11A illustrates a case where the wireless probe Probe 1 is selected to be preferentially connected to the ultrasound diagnosis apparatus 500 as indicated by reference numeral 1120.

When scanning of an object begins after setting of wireless probes is completed, the controller 510 may automatically perform the first communication connection 592 with the set wireless probe Probe 1. When the second event occurs, the controller 510 may automatically restore the first communication connection 592 with the set wireless probe Probe 1.

When the external apparatus setting menu 1032 is selected, the UI screen image 1150 of FIG. 11B may be output and displayed.

Referring to FIG. 11B, the UI screen image 1150 may include a list 1160 of external apparatuses which are configured for communicating with the ultrasound diagnosis apparatus 500. In detail, a case in which the ultrasound diagnosis apparatus 500 communicates with an external apparatus by using a Wi-Fi communication module based on Wi-Fi or WFD communication technology and the external apparatus includes an AP as described above with reference to FIG. 4 is illustrated. The local area communication module 531 performs an AP search to search for connectable external apparatuses Medical Device 1 and Medical Device 2. Then, the controller 510 may control the UI screen image 1150 including the list 1160 of the external apparatuses Medical Device 1 and Medical Device 2 that is connectable external apparatuses found by the local area communication module 531 so that the UI screen image 1150 may be output. Accordingly, the display 550 may display the UI screen image 1150 which includes the list 1160 of the connectable external apparatuses.

A user may select an external apparatus which is configured to be connected by default to the ultrasound diagnosis apparatus 500, by using the displayed UI screen image 1150.

FIG. 11B illustrates a case in which the external apparatus Medical Device 1 is selected to be preferentially connected to the ultrasound diagnosis apparatus 500 as indicated by reference numeral 1170.

When the first event occurs after setting of external apparatuses is completed, the controller 510 may automatically restore the first communication connection 597 with the set external apparatus Medical Device 1.

When the transmission setting menu 1033 is selected, the UI screen image 1200 of FIG. 12 may be output and displayed.

The UI screen 1200 may include a menu window 1210 for setting wireless probes which are configured to be connected via the first communication connection 592 and external apparatuses which are configured to be connected via the second communication connection 597, when the first communication connection 592 and the second communication connection 597 are automatically switched with each other.

Wireless probes 1220 which are configured to be connected via the first communication connection 592 may be wireless probes which are connectable to the ultrasound diagnosis apparatus 500. External apparatuses 1230 which are configured to be connected via the second communication connection 597 may be external apparatuses which are connectable to the ultrasound diagnosis apparatus 500.

In FIG. 12, the wireless probes Probe 1, Probe 2, and Probe 3 are found as the wireless probes 1220 which are connectable to the ultrasound diagnosis apparatus 500 and medical devices Med 1, Med 2, and Med 3 are found as the external apparatuses 1230 which are connectable to the ultrasound diagnosis apparatus 500. Moreover, in FIG. 12, the wireless probe Probe 1 is selected as a wireless device which is configured to be automatically changed, as indicated by reference numeral 1221, and the medical device Med 1 is selected as an external apparatus which is configured to be automatically changed, as indicated by reference numeral 1231.

Figure 13:
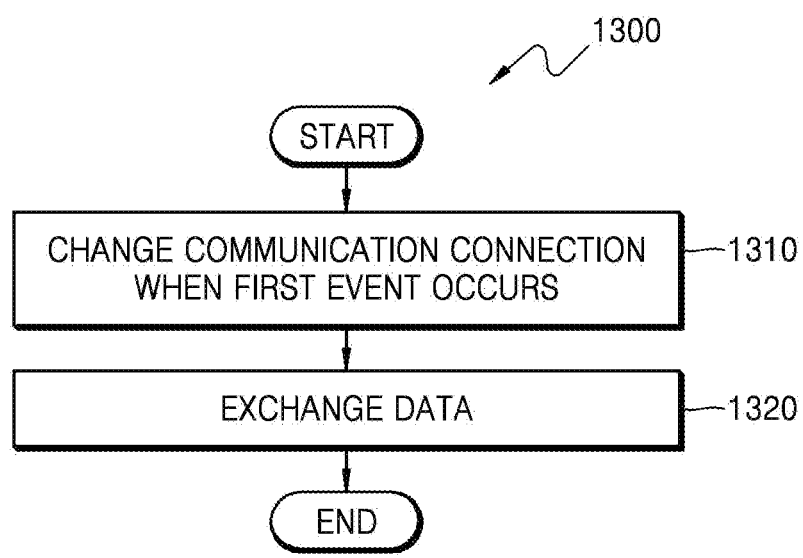
FIG. 13 is a flowchart of a communication connecting method performed in an ultrasound diagnosis apparatus, according to an exemplary embodiment.

FIG. 13 is a flowchart of a communication connecting method 1300 which is performable by using an ultrasound diagnosis apparatus, according to an exemplary embodiment. The communication connecting method 1300 has the same technical spirit as the ultrasound diagnosis apparatus 500 described above with reference to FIGS. 1-12. Accordingly, a repeated description of matters described above with reference to FIGS. 1-12 is omitted herein. The communication connecting method 1300 will now be described with reference to the ultrasound diagnosis apparatus 500.

Referring to FIG. 13, the communication connecting method 1300 is performed by using the ultrasound diagnosis apparatus 500 which is capable of being connected with the wireless probe 590, which is configured to acquire first data by scanning an object.

In operation 1310 of the communication connecting method 1300, when a first event occurs, the occurrence of the first event is recognized, and thus the first communication connection 592 with the wireless probe 590 via a first communication network is automatically terminated and the second communication connection 597 with the external apparatus 595 via the first communication network is automatically started. Operation 1310 may be performed by the first communicator 530 of the ultrasound diagnosis apparatus 500 under the control of the controller 510 of the ultrasound diagnosis apparatus 500.

In operation 1320, data is exchanged with the wireless probe 590 and/or with the external apparatus 595 via the first and/or second communication connection 592 or 597 that uses the first communication network. Operation 1320 may be performed by the first communicator 530 under the control of the controller 510.

As described above, according to the one or more of the above-described exemplary embodiments, when an ultrasound diagnosis apparatus is required to exchange data with a plurality of electronic apparatuses, which are a wireless probe and an external apparatus, by using a single communication module, communication connection may be flexibly changed based on respective operational situations of the wireless probe, the external apparatus, and the ultrasound diagnosis apparatus. Therefore, convenience and efficiency with respect to the ultrasound diagnosis apparatus exchanging data with the wireless probe and the external apparatus may increase.

The exemplary embodiments should be considered in descriptive sense only and not for purposes of limitation. Descriptions of features or aspects within each exemplary embodiment should typically be considered as available for other similar features or aspects in other exemplary embodiments.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

What is claimed is:

1. An ultrasound diagnosis apparatus connectable to a wireless probe that acquires first data by scanning an object, the ultrasound diagnosis apparatus comprising:
   a memory storing instructions; and
   a processor configured to execute the instructions to:
      in response to the scanning of the object being started, control to activate a first communication connection to the wireless probe via a communication network, to receive the first data from the wireless probe;
      recognize an occurrence of a first event that occurs when the wireless probe stops the scanning of the object;
      in response to the occurrence of the first event being recognized:
         automatically terminate the first communication connection to the wireless probe via the communication network; and
         automatically start a second communication connection to an external apparatus that is different from the wireless probe, via the communication network, to transmit second data corresponding to the first data to the external apparatus; and
      control to communicate with the external apparatus, via the second communication connection,
   wherein the memory is configured to store termination information including either one or both of status information relating to a communication with the wireless probe at a first point of time when the first communication connection terminates and data information relating to the first data that is received from the wireless probe before the first point of time, and
   wherein the processor is further configured to execute the instructions to, in response to the second communication connection being terminated and the first communication connection being restored, control to receive, from the wireless probe, subsequent data that is acquired subsequent to the first data, based on the termination information.

2. The ultrasound diagnosis apparatus of claim 1, wherein the occurrence of the first event is based on an operational status of any one or any combination of the wireless probe, the ultrasound diagnosis apparatus, and the external apparatus.

3. The ultrasound diagnosis apparatus of claim 1, wherein the first event occurs when the first data is not received by the ultrasound diagnosis apparatus after the first data is acquired by the wireless probe.

4. The ultrasound diagnosis apparatus of claim 1, wherein the first event occurs when a determination that the ultrasound diagnosis apparatus is not required to receive the first data is made.

5. The ultrasound diagnosis apparatus of claim 1, wherein the first event occurs when the wireless probe fails to scan the object for at least a predetermined interval of time.

6. The ultrasound diagnosis apparatus of claim 1, further comprising a display,
wherein the processor is further configured to execute the instructions to:
control the display to display an ultrasound image corresponding to the first data; and
in response to the occurrence of the first event being recognized, the first event occurring when the display of the ultrasound image terminates, control the display to display a screen image that does not include the ultrasound image, or display a still image.

7. The ultrasound diagnosis apparatus of claim 1, wherein the first event occurs when a manipulation of a user is not sensed for a predetermined period of time or the ultrasound diagnosis apparatus enters a standby mode.

8. The ultrasound diagnosis apparatus of claim 1, further comprising a user interface device,
wherein the processor is further configured to execute the instructions to receive a user input via the user interface device, and
wherein the first event occurs in response to a scanning stop request that being received from a user via the user interface device or a transmit request to transmit data to the external apparatus being received from the user via the user interface device.

9. The ultrasound diagnosis apparatus of claim 1, wherein the first event occurs in response to:
a terminate request to terminate transmission of the first data, the terminate request being received via the wireless probe; or
a transmit request to transmit data to the external apparatus, the transmit request being received via the wireless probe; or
a scanning stop request that is received via the wireless probe.

10. The ultrasound diagnosis apparatus of claim 1, wherein the memory is configured to store the first data that is received from the wireless probe,
wherein the first event occurs when the memory stores the first data and a first ultrasound image corresponding to the first data is generated under a control of the processor, and
wherein the first event occurs in response to a request for a review mode in which the first ultrasound image that is previously stored in the memory is displayed, being received from a user.

11. The ultrasound diagnosis apparatus of claim 1, wherein the processor is further configured to execute the instructions to, when the second communication connection starts, transmit, to the external apparatus, the first data and the second data including at least one ultrasound image from among a plurality of ultrasound images corresponding to the first data.

12. The ultrasound diagnosis apparatus of claim 11, wherein the processor is further configured to execute the instructions to:
terminate the second communication connection, and restart the first communication connection, when a transmission of the second data is completed, a scanning stop request that is previously received by either one or both of the wireless probe and the ultrasound diagnosis apparatus is canceled, a scan request to scan the object is received, the second data that is exchanged between the ultrasound diagnosis apparatus and the external apparatus is completed, or a medical worklist (MWL) is received from the external apparatus via the second communication connection.

13. The ultrasound diagnosis apparatus of claim 1, wherein the processor is further configured to execute the instructions to:
recognize an occurrence of a second event; and
in response to the second event being recognized, terminate the second communication connection, and restore the first communication connection.

14. The ultrasound diagnosis apparatus of claim 13, wherein the second event occurs when a determination is made that a first data exchange between the ultrasound diagnosis apparatus and the wireless probe is required, and
wherein the second event occurs based on an operational status of any one or any combination of the wireless probe, the ultrasound diagnosis apparatus, and the external apparatus.

15. The ultrasound diagnosis apparatus of claim 1, wherein the communication network is based on either one or both of a wireless fidelity (Wi-Fi) communication standard and a WiFi-direct (WFD) communication standard.

16. The ultrasound diagnosis apparatus of claim 1, wherein the memory is configured to store first setting information relating to the first communication connection, and store second setting information relating to the second communication connection,
wherein the processor is further configured to execute the instructions to control to:
automatically start the first communication connection, using the first setting information; and
automatically start the second communication connection, using the second setting information.

17. A communication connecting method performable by an ultrasound diagnosis apparatus connectable to a wireless probe that acquires first data by scanning an object, the communication connecting method comprising:
in response to the scanning of the object being started, controlling to activate a first communication connection to the wireless probe via a communication network, to receive the first data from the wireless probe;
recognizing an occurrence of a first event that occurs when the wireless probe stops the scanning of the object;
in response to the occurrence of the first event being recognized;
automatically terminating the first communication connection to the wireless probe via the communication network; and
automatically starting a second communication connection to an external apparatus that is different from the wireless probe, via the communication network, to transmit second data corresponding to the first data;

controlling to communicate with the external apparatus, via the second communication connection;

storing termination information including either one or both of status information relating to a communication with the wireless probe at a first point of time when the first communication connection terminates and data information relating to the first data that is received from the wireless probe before the first point of time; and in response to the second communication connection being terminated and the first communication connection being restored, controlling to receive, from the wireless probe, subsequent data that is acquired subsequent to the first data, based on the termination information.

* * * * *